(12) United States Patent
Kurtz et al.

(10) Patent No.: US 7,460,248 B2
(45) Date of Patent: Dec. 2, 2008

(54) TISSUE IMAGING SYSTEM

(75) Inventors: Andrew F. Kurtz, Macedon, NY (US);
Joseph R. Bietry, Rochester, NY (US);
Paul O. McLaughlin, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 302 days.

(21) Appl. No.: 11/383,254

(22) Filed: May 15, 2006

(65) Prior Publication Data

US 2007/0263226 A1  Nov. 15, 2007

(51) Int. Cl.
*G01B 9/02* (2006.01)
*G01B 11/02* (2006.01)

(52) U.S. Cl. .................. 356/521; 356/495; 356/497; 356/512

(58) Field of Classification Search ................. 356/521, 356/479, 497, 490, 495, 511, 512
See application file for complete search history.

(56) References Cited

U.S. PATENT DOCUMENTS

| | | | |
|---|---|---|---|
| 2,403,731 A | 7/1946 | MacNeille | |
| 3,013,467 A | 12/1961 | Minsky | |
| 4,802,748 A | 2/1989 | McCarthy et al. | |
| 5,032,720 A | 7/1991 | White | |
| 5,067,805 A | 11/1991 | Corle et al. | |
| 5,353,799 A | 10/1994 | Chance | |
| 5,459,570 A | 10/1995 | Swanson et al. | |
| 5,587,832 A | 12/1996 | Krause | |
| 5,659,392 A | 8/1997 | Marcus et al. | |
| 5,782,237 A | 7/1998 | Casciani et al. | |
| 5,784,189 A | 7/1998 | Bolzer et al. | |
| 5,859,808 A * | 1/1999 | Campbell et al. | 365/216 |
| 5,867,251 A | 2/1999 | Webb | |
| 5,923,466 A | 7/1999 | Krause | |
| 5,978,136 A | 11/1999 | Ogawa et al. | |
| 5,983,120 A | 11/1999 | Groner et al. | |
| 6,034,774 A | 3/2000 | Marcus et al. | |
| 6,073,045 A | 6/2000 | Dyson et al. | |
| 6,122,103 A | 9/2000 | Perkins et al. | |
| 6,144,489 A | 11/2000 | Wilson et al. | |

(Continued)

OTHER PUBLICATIONS

Kolarova et al.; Penetration of the Laser Light Into the Skin In Vitro; Lasers in Surgery and Medicine 24:231-235 (1999).

(Continued)

*Primary Examiner*—Patrick J Connolly

(57) ABSTRACT

A tissue imaging system (200) for examining the medical condition of tissue (290) has an illumination optical system (205), which comprises a light source (220), having one or more light emitters, beam shaping optics, and polarizing optics. An optical beamsplitter (260) directs illumination light to an imaging sub-system, containing a spatial light modulator array (300). An objective lens (325) images illumination light from the spatial light modulator array to the tissue. An optical detection system (210) images the spatial light modulator to an optical detector array. A controller (360) drives the spatial light modulator to provide time variable arrangements of on-state pixels. The objective lens operates in a nominally telecentric manner relative to both the spatial light modulator and the tissue. The polarizing optics are independently and iteratively rotated to define variable polarization states relative to the tissue. The modulator pixels optically function like pinholes relative to the illumination light and the image light.

91 Claims, 15 Drawing Sheets

U.S. PATENT DOCUMENTS

| | | | |
|---|---|---|---|
| 6,208,415 B1 | 3/2001 | DeBoer et al. | |
| 6,243,199 B1 | 6/2001 | Hansen et al. | |
| 6,248,988 B1 * | 6/2001 | Krantz | 250/201.3 |
| 6,399,935 B1 | 6/2002 | Jovin et al. | |
| 6,421,163 B1 * | 7/2002 | Culver et al. | 359/279 |
| 6,438,396 B1 | 8/2002 | Cook et al. | |
| 6,483,641 B1 * | 11/2002 | MacAulay | 359/385 |
| 6,532,111 B2 | 3/2003 | Kurtz et al. | |
| 6,577,884 B1 | 6/2003 | Boas | |
| 6,585,378 B2 | 7/2003 | Kurtz et al. | |
| 6,600,474 B1 | 7/2003 | Heines et al. | |
| 6,615,072 B1 | 9/2003 | Izatt et al. | |
| 6,650,916 B2 | 11/2003 | Cook et al. | |
| 6,769,769 B2 | 8/2004 | Podoleanu et al. | |
| 6,876,494 B2 * | 4/2005 | Ishikawa et al. | 359/618 |
| 6,909,473 B2 | 6/2005 | Mi et al. | |
| 6,927,860 B2 | 8/2005 | Podoleanu et al. | |
| 6,940,602 B2 | 9/2005 | Dubois | |
| 6,975,786 B1 * | 12/2005 | Warr et al. | 385/17 |
| 2003/0021016 A1 * | 1/2003 | Grier | 359/368 |
| 2004/0147808 A1 * | 7/2004 | MacAulay et al. | 600/160 |
| 2005/0168823 A1 * | 8/2005 | Ishii et al. | 359/626 |
| 2007/0188856 A1 * | 8/2007 | MacAulay | 359/385 |
| 2007/0263226 A1 * | 11/2007 | Kurtz et al. | 356/492 |

OTHER PUBLICATIONS

Nickell et al.; Anisotropy of light propagation in human skin; Phys. Med. Biol. 45 (2000), pp. 2873-2886.

Xu et al.; Confocal enhanced optical coherence tomography for nondestructive evaluation of paints and coatings; Optics Letters, vol. 24, No. 24, Dec. 15, 1999, pp. 1808-1810.

* cited by examiner

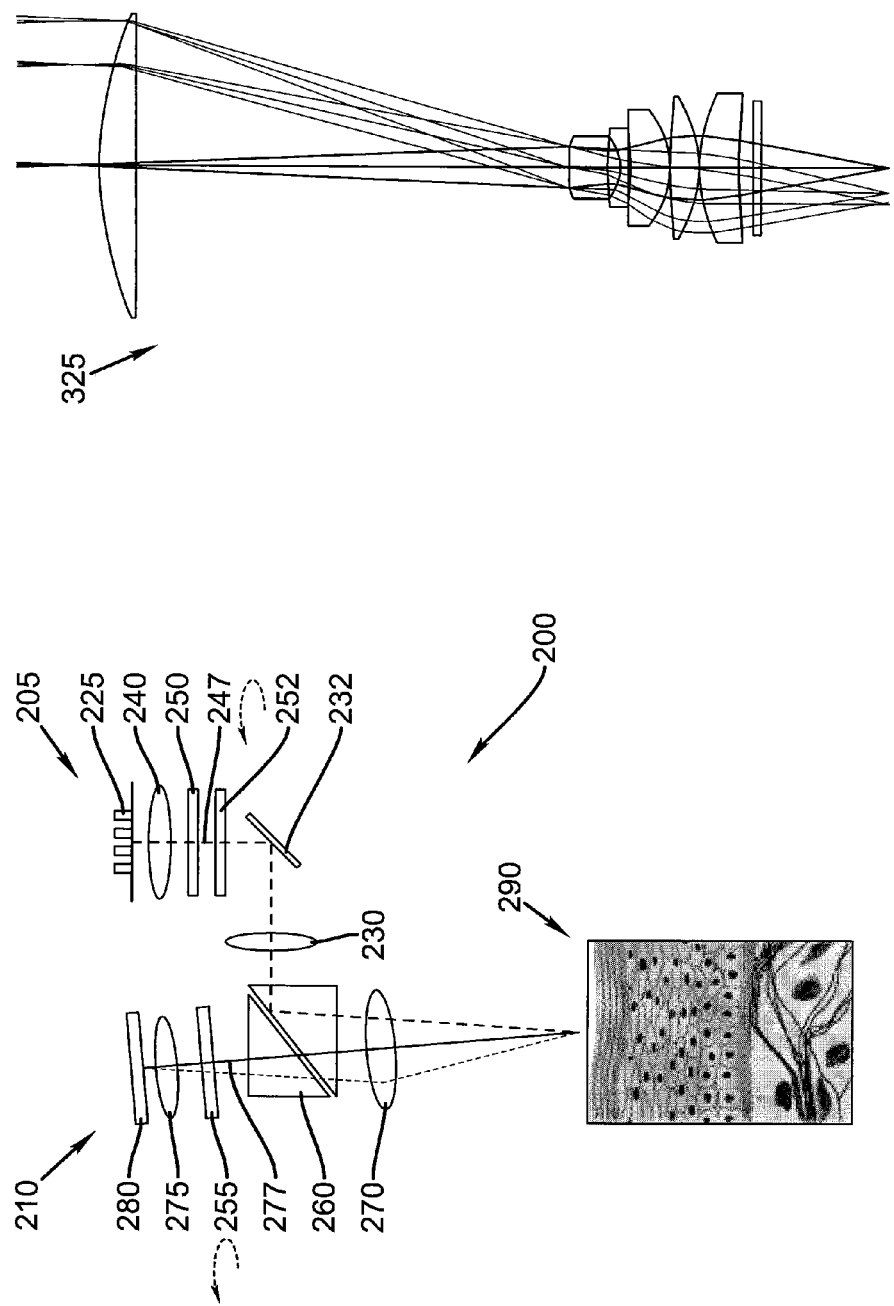

TISSUE IMAGING SYSTEM

CROSS REFERENCE TO RELATED APPLICATIONS

Reference is made to commonly-assigned copending U.S. patent application Ser. No. 11/087,183 filed Mar. 23, 2005, entitled WOUND HEALING MONITORING AND TREATMENT, by Kurtz, the disclosure of which is incorporated herein.

FIELD OF THE INVENTION

This invention relates in general to an optical based medical imaging system designed for the examination of tissues, in which the system provides illumination light and then collects return light that is imaged to a sensor array. In particular, the invention relates to a modulator based optical imaging system that is optimized for imaging structures within tissue, and within tissue wounds in particular.

BACKGROUND OF THE INVENTION

In general, the healing of wounds, burns, and other injuries is an uncertain endeavor. The clinician cannot be certain about the condition of the tissue being treated, the efficacy of treatments, and whether further treatments or a change in treatments is appropriate. As a particular example, many chronic wounds, such as pressure ulcers or venous stasis ulcers often linger for months or even years, despite the various treatments being applied. These wounds are particularly intractable for a variety of reasons; with age, nutrition, diabetes, infection, marginalized immune systems, and other factors, contributing to the ongoing difficulties in healing. In most cases, such wounds are chronic because the wound healing is stalled relative to one or more aspects of the process. In such circumstances, it is not unusual for the clinician to be unsure about the status of the wounded tissue, at what point in wound healing the tissue is held up, and what new treatment modality should be applied.

In general, the detection and diagnosis of deep tissue injuries (chronic wounds, bruises, surgical wound complications, sports injuries, etc.) is difficult. There are a variety of methods and devices that can be utilized to aid ongoing diagnosis. For example, tissue biopsies can be taken, and used in tissue cultures and histology. These traditional methods are disadvantaged by the time delay in evaluating tissue cultures or histology, which easily can be a week or two. Additionally, these approaches are invasive, and actually cause further damage to the tissue. As histology relies on thin slices of tissue, which are dyed and examined optically with a microscope, histology typically only provides a direct indication of the tissue structure in two-dimensions.

Alternate technologies have been developed for non-invasive histology or tissue imaging, including X-ray, magnetic resonance imaging (MRI and NMR), computed axial tomography (CAT) scanning, and positron emission tomography (PET). These technologies are used for a variety of applications (mammography, brain scans, etc.), but are seldom used for examining soft tissue wounds, and can expose the patient to high-energy radiation (x-rays, etc.). Ultrasound, which is widely used for pre-natal examination, can also be used for examining wounds. In particular, Longport Inc. (Glen Mills, Pa.) offers a high frequency (20 MHz) ultrasound scanner, described in U.S. Pat. No. 6,073,045 (Dyson et al.) that scans tissue to modest depths (2 cm) but with "high" spatial resolution (65 microns).

However, because many biological structures, including cells, are much smaller than 65 microns, there is a need for other imaging technologies that offer higher resolution, but at a lower cost than MRI and some other medical imaging technologies. There are a variety of technologies, including confocal scanning microscopy, optical coherence tomography (OCT), diffuse optical tomography (DOT), second harmonic generation (SHG) and multi-photon based microscopy, which apply optical techniques to obtain high resolution images either in-vivo or in-vitro. In these cases, imaging resolution can be a few microns or less, which certainly enables detection of much finer structures than does ultrasound. On the other hand, light absorption and scatter limit the imaging depth in most tissues to only ~1-4 mm. While many of these systems have been used for optical histology, providing a two-dimensional image of the tissue, newer technologies, such as full field OCT systems, enable three-dimensional images. Although these various optical imaging technologies are being used for both research and clinical diagnosis, in general there are opportunities for improvements to facilitate wider diagnostic use, including the application in wound assessment.

It appears that the ideal diagnostic device for diagnostic assessment of deep tissue injuries does not yet exist. Such a device would provide sharp and clear images with an imaging resolution of 2-5 µm within a relatively deep imaging depth of 1-5 cm, while covering a sizeable imaging area of 1-100 $cm^2$, with a cost of $10,000-$50,000, depending on features. There are some emerging technologies, such as terahertz imaging or the "NMR Mouse," which may yet fulfill this need. However, lacking such a definitive technical solution, then it appears that dual modality devices offer the greatest potential. For example, a dual ultrasound and optical imaging system may work, if these imaging modalities could be synergistically and inexpensively combined. Alternately, there appears to be opportunity in multi-modal optical devices, which combine various optical imaging modalities (such as photographic imaging, confocal microscopy, OCT, or DOT) in one device. As these various technologies all manipulate light to create images, judicious design choices could facilitate useful combinations. Even so, optical imaging in scattering tissues is then necessarily limited to imaging depths in the 1-6 mm range. Nonetheless, imaging within that depth range could still have considerable value.

Obviously the device requirements derive from the physiological and optical properties of the tissues in question. In the particular case of wound assessment, it is necessary to understand both the physiobiology and the optical properties of wounds. As wounds heal, they normally progress through a sequence of overlapping interactive phases, starting with coagulation and progressing through inflammation, proliferation (which includes granulation, angiogenesis, and epithelialization), and remodeling.

Success in wound healing is very much dependent on the rebuilding of the extra-cellular matrix (ECM), which is initially dependent on fibroblasts. Fibroblasts migrate into the wound site, and begin to build the ECM by depositing a protein called fibronectin. Fibronectin is deposited with some directionality, mirroring the axis of the fibroblasts. The fibroblasts then produce collagen, with the collagen deposition generally aligned to the fibronectin pattern. Over time, fibronectin is replaced by Type III collagen and ultimately by Type I collagen. In parallel, angiogenesis occurs, and new capillaries bud and grow into the collagen network, creating granulation tissue. Over time, granulation tissue continues to change, attempting to become as much like normal tissue as possible. For example, as the wound contracts, and is subsequently remodeled and influenced by stresses from neighboring tissues, the collagen becomes increasingly organized. Even late in the remodeling phase, which can end six months to a year post injury, collagen in a scar will be replaced and rearranged as the wound attempts to regain its original function.

In considering the in-vivo optical imaging of wounds, the fact that both collagen and capillaries are optically birefringent, represents an opportunity to monitor the wound healing processes involving the formation and remodeling of the extra-cellular matrix (ECM) and granulation tissue. Obviously, a medical optical imaging system could have polarization sensitivity to help see these features. Additionally however, granulation tissues and wound tissues have other attributes, such as altered optical transmission properties and cellular and extra-cellular morphologies which could effect optical imaging therein, which a properly design medical imaging system could utilize, if it were designed correctly.

As mentioned previously, various optical technologies (confocal microscopy, OCT, SHG, fluoroscopy, diffuse optical tomography) and combinations thereof have been developed for use in medical tissue imaging. Confocal microscopy and OCT are particularly of interest, as these two technologies have been specifically developed to enable optical imaging "deep" into tissue, which is a turbid media in which scattering severely limits the potential for tissue imaging. Both confocal microscopes and OCT systems are often designed to image sub-cellularly, so that internal cellular structures such as the nuclei and mitochondria can be examined. To provide the desired submicron (~0.2-1.0 µm) resolution, these systems utilize very fast optics (Numerical Aperture (NA) ~0.8-1.4), often enabled by immersion optics. As a result, both the field of view and imaging depth of such systems are constrained, thereby limiting the in-vivo imaging utility of these devices.

Presently, OCT systems are used more widely than are confocal imaging systems, because they can image to greater depths (~2-3×) into tissues. However, as tissue scattering limits OCT imaging, the technology has been most successfully applied in ocular applications, where the tissue is weakly scattering, to examine visual pathologies such as glaucoma, diabetic retinopathy, macular degeneration, etc. In particular, the coherence/interference effect utilized by OCT provides greater signal discrimination (rejection of out of focus light) than does confocal microscopy, which relies on one or more pinholes for signal discrimination. In general, an OCT system is basically a fiber optic based interferometer, typically using a low coherence (broad band, for example ~30-70 nm) light source. Such systems are provided with a sampling arm, which includes a fiber optic probe to direct light onto the tissue. These system also have a reference fiber optic arm with a retro-reflector. The interference effect between the sample arm light and the reference arm light allows OCT systems to control the depth of focus, so that a small longitudinal distance is in focus. Images are constructed by first measuring the in-depth profile of the backscattered light intensity in the axial (depth) direction. This backscattered light is predominately that from a single scattering event, with a lesser contribution from light that encountered small angle scattering events. In-depth profiling is performed by measuring the echo time delay and intensity of backscattered or reflected light. Distance or spatial information is determined from the time delay of reflected echoes. To create a two-dimensional image, the fiber optic beam is moved laterally across the surface (x-axis) and in-depth profiles (z-axis) are obtained at discrete points along the surface. The net result is that the resolution (1-20 microns) and dynamic range of the sample are in-focus and enhanced as compared to the portion of the sample the un-focused beam traveled through. This can be particularly advantageous for imaging in turbid, light scattering optical media, such as tissue. However, OCT imaging depth and resolution, and signal strength are all effected by the scattering properties of the tissue being examined. In general, the less scattering there is (smaller scattering coefficient, µs), the deeper the imaging. However, the directionality of the scattering (forward or back) also effects signal strength, signal localization, and resolution. Exemplary OCT system patents include U.S. Pat. Nos. 5,659,392 and 6,034,774 (both to Marcus et al.), both of which are assigned to the same assignee as the present invention.

Polarization sensitive OCT systems have also been developed. An exemplary prior art system, described in U.S. Pat. No. 6,208,415 (DeBoer et al.), has been used at Massachusetts General Hospital to examine dermal tissues, burns, scars, and tendons. Another exemplary prior art OCT system, described in U.S. Pat. No. 6,615,072 (Izatt et al.) is equipped with a polarization compensation system, so as to desensitize the device to polarization degradation effects that occur in bent single mode optical fibers. Another similar system is a polarization sensitive low coherence reflectometer, such as described in U.S. Pat. No. 5,459,570 (Swanson et al.) which has 11 micron resolution and 120 dB signal to noise ratio. Although the fiber optic OCT systems can have a small probe for in-vivo testing, these systems are complicated and expensive, and are not likely to be used by a clinician in wound assessment either in the field or in many clinical settings.

OCT systems can also be designed with more traditional optics (rather than fiber optics), by combining the attributes of a Michelson interferometer with those of a microscope. In particular, wide field (or full field) of view OCT systems have been developed, wherein a microscope objective lens is used to illuminate and image the sample, while a second lens is placed in the reference arm of the interferometer. An exemplary wide field OCT system is described in U.S. Pat. No. 6,940,602 (Dubois). While OCT systems are advantaged over confocal systems relative to imaging depth and depth resolution, the systems are more complicated (with the reference arm) and potentially less flexible.

In confocal microscopy, light is directed through a pinhole to create a spot of light, which is projected or imaged into the sample under examination. Returning, backscattering image light is imaged to a pinhole stop located in an intermediate image plane. The image light is directed to a sensor, to provide data signals. As a result, only light from the focal plane can reach the detector. Other potential image locations within the sample, such as out-of-focus planes or spatially offset locations within the same plane are blocked out, as the spatial filtering effect of the pinhole acts as an intensity-gate. This results in an "optical section." With the confocal microscope, the z-resolution, or optical sectioning thickness, depends on a number of factors, including wavelength $\lambda$, pinhole size, numerical aperture (NA) of the objective lens, refractive index (n) of the components, and the alignment of the instrument. Whereas, viewing depth largely depends on tissue scattering and absorption properties and pinhole size.

The confocal microscope, as described in U.S. Pat. No. 3,013,467, was originally developed by Marvin Minsky as an approach to examine each point of a specimen and measure the amount of light scattered or absorbed by that point, while minimizing the collection and detection of light scattered by neighboring points. Most simply, confocal microscopes are constructed with a single pinhole that defines both the size of the illumination light that will be imaged to the tissue, and the size of the spot of return light allowed to reach the detector. Alternately, the optical design can provide separate pinholes in the illumination and imaging paths. However, the price of single-point illumination is being able to measure only one point at a time. Thus, in a traditional confocal microscope, the specimen is scanned point by point and the resulting image is reconstructed thereafter. The sample can be moved relative to the microscope either by laterally translating the sample itself (with translation stages) or sweeping (with galvanometers) the illuminating light beam over the sample.

However, the utility of confocal microscopes can be limited by weak signals. Compared to a normal microscope, the amount of light that is seen in the final image is greatly reduced by the pinhole, sometimes up to 90-95%. To compensate for this loss of light somewhat, lasers are used as light sources instead of the conventional mercury arc lamps because they produce extremely bright light at very specific wavelengths. As an example, U.S. Pat. No. 5,032,720 (White) describes a beam scanning confocal fluorescence microscope in which the light emitted from an argon laser is focused to the sample, and the coherence of the laser allows it to act as its own pinhole, so that an illuminating pinhole is not needed. As a result, the optical system has greater optical efficiency, and stronger signals will be available at the detector.

As one approach to increase the throughput of a confocal microscope, both the stage and the light source can be kept stationary, while the specimen is scanned with an array of light spots transmitted through apertures. Alternately, a time variant array of light spots is created by spinning a Nipkow disk within the microscope assembly. For example, U.S. Pat. No. 4,802,748 (McCarthy et al.) describes a tandem scanning reflected light confocal microscope in which a Nipkow disc has a series of apertures located in an annular pattern of spiral arms on the disc surface. U.S. Pat. No. 5,067,805 (Corle) describes a polarization sensitive confocal scanning optical microscope with a spinning Nipkow disc in which the polarization beamsplitter is tilted relative to the optical system to prevent crosstalk from stray reflected light.

As an alternate approach to improving the throughput of a confocal microscope, systems have been developed wherein the mechanically rotating Nipkow disc has been replaced by a spatial light modulator array, which can be electrically addressed and thus function as a programmable pinhole array. In particular, U.S. Pat. No. 5,587,832 (Krause) describes a spatially light modulated confocal microscope in which a modulator array, such as a liquid crystal device (LCD), a digital micro-mirror device (DMD), or a micro-shutter array is image conjugate to the tissue and is operated to function as a programmable multi-pinhole generator. In the system of Krause '832, two modulator arrays, one for illumination, and a second for detection, are used in tandem, under the control of a central processor. While Krause '832 provides the basic elements of a modulator based confocal imaging system, the various approaches described therein lack optical design attributes (such as telecentricity, uniform flood illumination, and focus adjustments) that would improve the performance and utility of the concept. Additionally, the various designs lack the polarization sensitive optics, and control thereof, that would be useful in examining extra-cellular structures (such as collagen) in normal tissues (such as skin), wounded tissues, and granulation (healing) tissues. Krause '832 also does not consider a device with multiple imaging modalities that could be enabling for examining deep tissue injury.

In a second patent, U.S. Pat. No. 5,923,466 (Krause), another version of a spatially light modulated confocal microscope system is described, in which a single DMD array is used in dual roles as both the source pinhole generator and the detector pinhole generator. Within a large reflective optical system, used both in collection and detection. The system of Krause '466 is fairly complicated, using a dual Offner type reflective imaging optics and a single mode optical fiber couple laser source, and is not designed either for low cost and ease of use, nor for examining wounds and optically birefringent tissue structures.

U.S. Pat. No. 5,867,251 (Webb) describes a tandem scanning confocal ophthalmoscope utilizing two spatial light modulators to create an image of an object plane located within the interior of the eye. This system is similar to that of Krause '832, but is optimized for ocular diagnostic applications rather than for looking at skin, wounds, and birefringent tissue structures, and thus lacks many of the same attributes discussed with respect to Krause '832 above.

By comparison, U.S. Pat. No. 6,399,935 (Jovin et al.) attempts to improve upon Krause '832 by providing an alternate DMD-based programmable confocal microscope with improved light efficiency and dual confocal and non-confocal (conventional) microscopy capability. In particular, this patent uses the on-state pixels to collect the confocal image and the off-state pixels to collect the non-confocal image, using either two detector arrays or two light sources to provide the duality of use. Additionally, pseudorandom pixel patterns, for example based upon cyclic Hadamard matrices, are suggested as a means to improve capture speed and the effective light efficiency. U.S. Pat. No. 6,483,641 (MacAulay) describes further DMD-based programmable microscopes, but ones in which the modulator arrays are located in optical planes conjugate to the aperture stop of the system, rather than conjugate to the object and image planes of the system. In this instance, the intent is to provide rapid control of the angular spectrum of the illumination light that is incident to the sample. A further reference, U.S. Pat. No. 6,144,489 (Wilson), describes a confocal microscope in which an encoded mask is used in the illumination system with patterns to generate combined confocal and non-confocal images. The mask can be a spinning disc, or a spatial light modulator, such as a DMD or a ferroelectric liquid crystal device. Again, all of the above prior art devices lack the appropriate design attributes for a medical imaging system that is optimized for use in examining skin, wounds, deep tissue injury, and birefringent tissue structures.

Wilson has also reported the use of structured illumination to provide a wide field-of-view confocal-like optical sectioning capability, without using either a Nipkow disc or a modulator array to address the specimen. Alternately, some systems have been proposed, such as those described in U.S. Pat. Nos. 6,769,769 and 6,927,860 (both to Podoleanu et al.), in which both OCT and confocal microscopy are combined together in a dual modality instrument, so that both types of images can be captured sequentially or simultaneously. However, these devices utilize single point imaging and scanning, rather than an array imaging or wide field of view approach.

It is noted that some portable, non-OCT or non-confocally based, optical devices for tissue diagnosis using polarization optics have also been developed. As an example, Lekam Medical (Devon, United Kingdom) offers the Cytoscan, which uses orthogonal polarization spectral imaging technology developed by Cytometrics Inc., and described in a U.S. Pat. No. 5,983,120 (Groner et al.); U.S. Pat. Nos. 6,438,396 and 6,650,916 (both to Cook et al.). This system is designed to provide images of the micro-circulatory vascular network, and is not optimized to examine the collagen network present in the dermal layers of skin. The Cytoscan system does not provide the proper optical wavelengths, high contrast polarizers, polarization control, or depth imaging to properly examine wounds and granulation tissues.

In considering the need for tissue imaging systems, which would be appropriate for wound assessment and other similar purposes, and which would be capable of imaging tissue structures with large fields of view at various depths, with the option of polarization sensitivity, it is seen that the range of present devices do not fulfill the anticipated diagnostic needs. In particular, there are needs for design for compact multi-functional diagnostic medical imaging systems. There are also opportunities for improved medical imaging devices that offer a wide range of capabilities and operational modalities.

SUMMARY OF THE INVENTION

Briefly, according to one aspect of the present invention a tissue imaging system for imaging optically examines the medical condition of tissue comprises an illumination optical system, which comprises a light source, having one or more light emitters, beam shaping optics, and polarizing optics, which together provide illumination light. An optical beam-splitter accepts illumination light from the illumination system and directs it to an imaging sub-system, which contains a spatial light modulator array. An objective lens with a focus control means images illumination light from the spatial light modulator array to the tissue for collecting image light from the tissue and imaging the image light to the spatial light modulator array. An optical detection system includes focusing optics and polarizing optics which image the spatial light modulator to an optical detector array. A control drives the spatial light modulator to provide time variable arrangements of on-state pixels, wherein each of the on-state pixels transmits beams of illumination light. The objective lens operates in a nominally telecentric manner relative to both the spatial light modulator and to the tissue. The polarizing optics, provided in the illumination optical system and the optical detection system, are independently and iteratively rotated so as to define variable polarization states relative to the tissue. The spatial light modulator array is operated such that the modulator pixels optically function like pinholes relative to the illumination light and the image light.

The invention and its objects and advantages will become more apparent in the detailed description of the preferred embodiment presented below.

BRIEF DESCRIPTION OF THE DRAWINGS

FIG. 3 is a cross sectional view of a concept for a tissue imaging system from the cross-referenced copending U.S. patent application Ser. No. 11/087,183.

FIG. 4b is a cross-sectional view of a representative design for an objective lens for a tissue imaging system of the present invention.

DETAILED DESCRIPTION OF THE INVENTION

Figure 1:
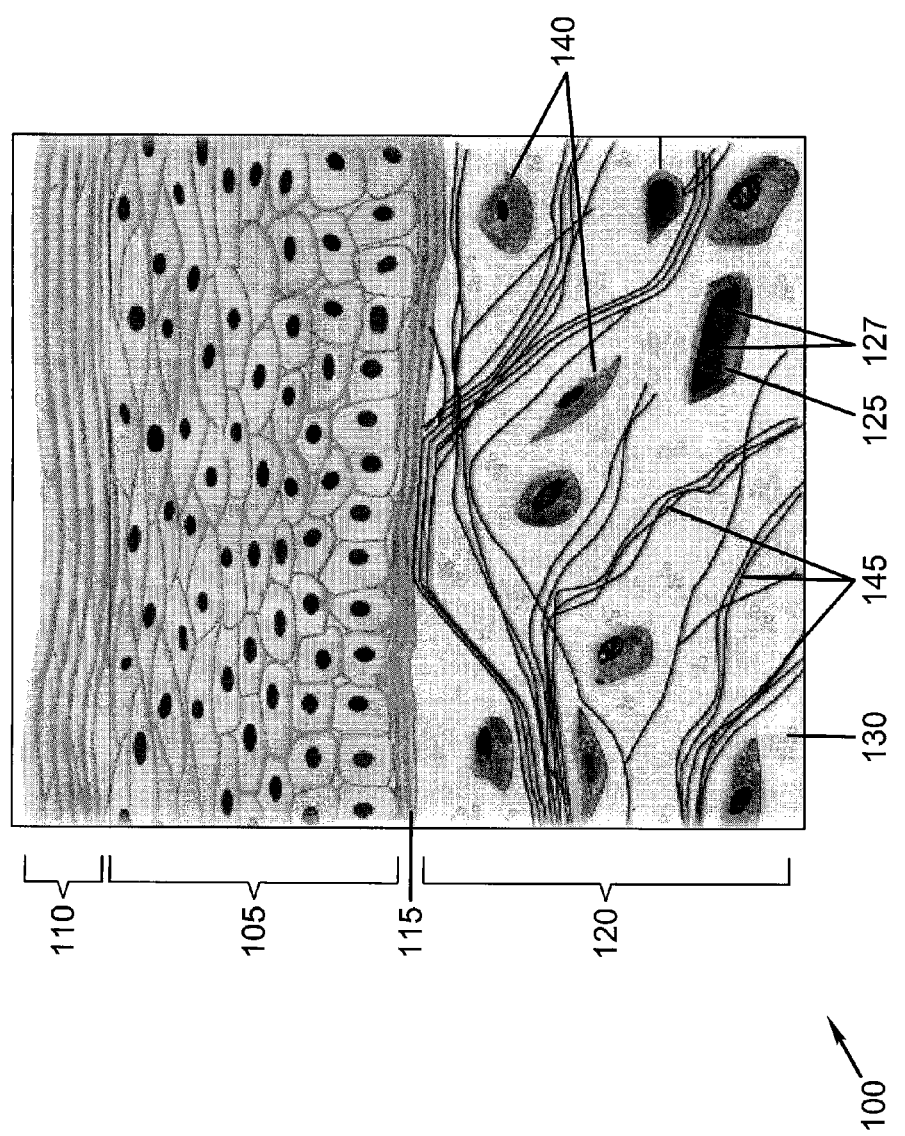
FIG. 1 is a cross-sectional view of the epidermal and dermal layers of the skin.

The following is a detailed description of the preferred embodiments of the invention, reference being made to the drawings in which the same reference numerals identify the same elements of structure in each of the several figures. The present invention is generally directed at providing an optical device appropriate for imaging deep tissue injuries, and in particular, for examining wounds and the surrounding tissues. As such, the device is intended to image a significant diagnostic area (for example ~1 $cm^2$) with a modest resolution (~4 µm) appropriate foe examining cellular morphology and extra-cellular structures. The device of the present invention also preferably enables multi-modal imaging in one device, as an approach to maximizing its diagnostic utility.

These goals can be best appreciated within the context of the biology of normal, wounded, and healed skin, and in particular, with respect to the function of fibroblasts and collagen. Accordingly, FIG. 1 depicts the cross-sectional composition of skin. Skin 100 (or the integument) covers the entire external surface of the human body and consists of two mutually dependent layers, the epidermis 105 and the dermis, which rest on a fatty subcutaneous layer, the panniculus adiposus (not shown). The epidermis 105, which is the outer layer of skin, is made up of epithelial cells (also known as squamous cells or keratinocytes), basal cells, and melanocytes. The outermost layer of the epidermis 105 comprises layers of dead epithelial cells 110. The basal cells are responsible for producing the epithelial cells, while the melanocytes produce pigments (melanin) that give skin its color. Below the epidermis 105 is the basement membrane 115 (also known as the basal lamina), which helps attach the epidermis 105 to the reticular dermis 120. The basal lamina 115 actually comprises several layers, and includes proteoglycans and glycoproteins as well as Type IV collagen. The innermost layer of the basal lamina 115 includes several types of fibrils, including collagen Type III and Type VII fibrils, which help anchor to the dermis. The dermis comprises several layers, including the papillary dermis (not shown) and the reticular dermis 120, which is the primary dermal layer. The papillary dermis is composed of fine networks of Types I and III collagen, elastic fibers, capillaries and fibroblasts. The reticular dermis 120 contains thick collagen bundles (thicker than the papillary dermis), which are generally arranged in layers parallel to the surface of the skin. In FIG. 1, the reticular dermis 120 is shown, with constituent blood capillaries 125 with transiting red blood cells 127, fibroblasts 140, collagen fiber bundles 145, and proteoglycans 130. Proteoglycans 130 are large molecules that attract and hold water, thereby providing cushioning and support. The reticular dermis 120 also contains other structures (not shown), such as elastin, sebaceous glands, sweat glands, hair follicles, and a small number of nerve and muscle cells.

The dermal skin layers vary with body location. For example, skin is quite thin on the eyelids, but is much thicker on the back and the soles of the feet. The epidermis ranges in thickness from ~30 microns to ~1 mm, while the dermis (papillary and reticular) ranges between ~300 microns and ~3 mm in thickness. The collagen structure in skin also varies with location, as will be discussed subsequently.

Fibroblasts create many of the components of the connective tissue in the reticular dermis, including the elastin, fibronectin, and collagen, which are all complex fibrous proteins. Collagen actually comprises long bundles or strands, composed of innumerable individual collagen fibrils. Fibroblasts synthesize collagen (both Type I and Type III), in a process beginning with procollagen, which is polymerized outside the fibroblasts to form tropocollagen, which in turn is formed into collagen fibrils and collagen bundles. The collagen fibril segments are ~25-50 microns in length and ~10-200 nm in diameter (depending on type). These fibril segments fuse linearly and laterally (crosslink) to form longer, thicker, biomechanically competent collagen fibrils within collagen bundles 145, which can be $200^+$ microns in length. Smaller collagen bundles can be 0.5-10 microns in diameter, although thicker bundles, particularly in the reticular dermis, can be ~100 microns in diameter. Notably, Type III collagen fibers are generally thinner than the Type I fibers.

Figure 2C:
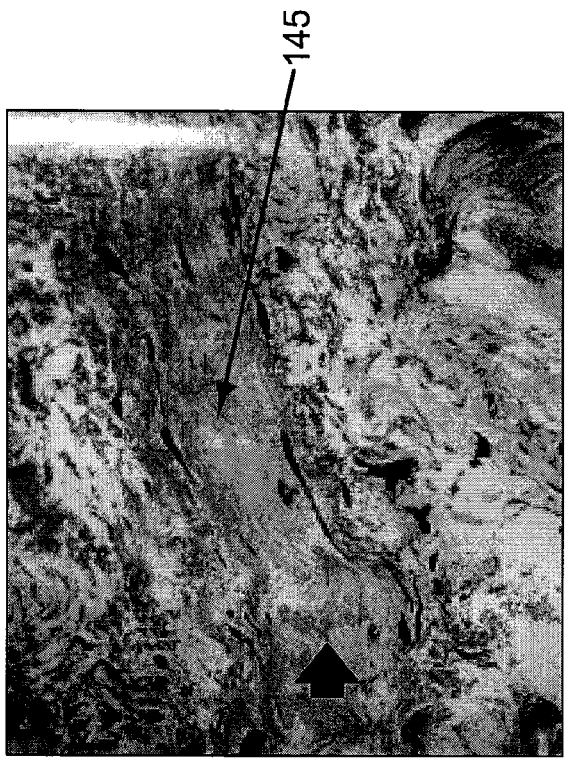
FIGS. 2a and 2c are two histological cross-sectional pictures showing collagen structures in skin.
Figure 2A:
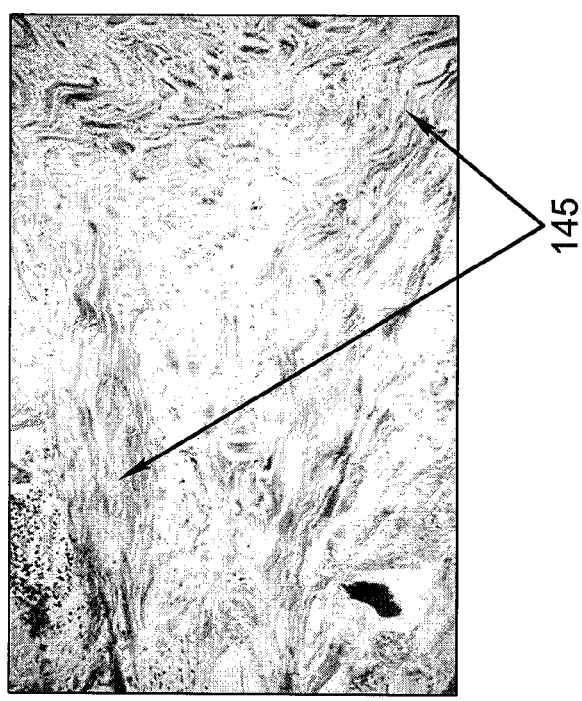
Figure 2B:
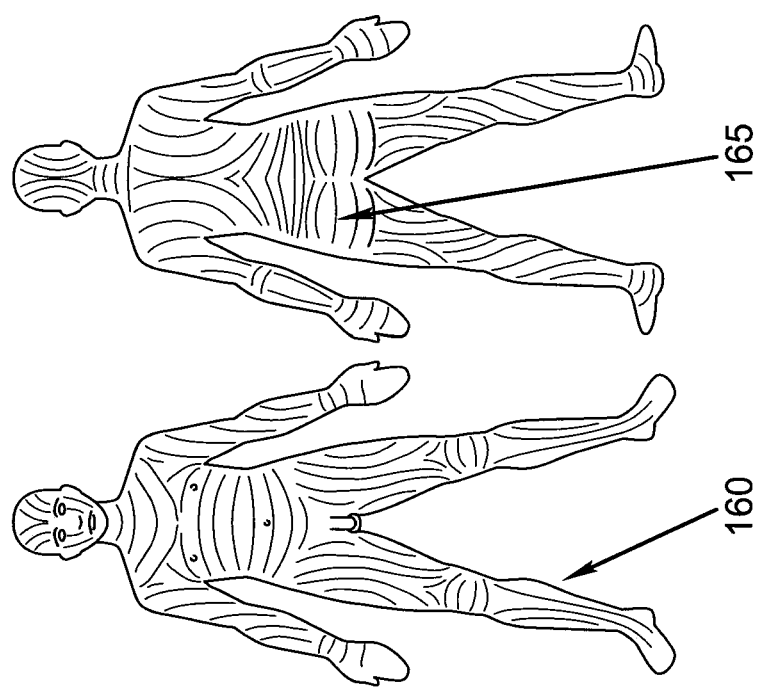
FIG. 2b is an illustration of Langer's cleavage lines.

The most structured collagen formations are found in bones and tendons. The collagen structures in tendons, ligaments, and vocal cords, which are termed "dense regular" and have collagen fibers in parallel alignment, are structured to handle stresses and transmit forces along their length. By comparison, the collagen structures in skin (see FIG. 2a), in which the collagen fibrils and bundles are less organized and somewhat wavy or convoluted, are termed "dense irregular." Although some researchers have described the collagen structures in skin to be random or haphazard, there is both local and macro patterning. Human dermal tissue (skin) is compliant and adapts to pressures from all directions. The collagen network, which is multi-directional and multi-layered, is an interwoven mesh generally parallel to the surface of the skin, which gives skin its toughness and adaptability. However, there is a pre-dominant direction to the orientation of the fiber bundles in a given location. As shown in FIG. 2b, Langer's cleavage lines 165 are generally associated with the alignment of collagen bundles deep in the reticular dermis. These lines portray the directional effects of skin across the human body 160, wherein the stress-strain relationships in uniaxial tension show skin to be stiffer along Langer's lines than across the lines. Langer's lines 165 are used as guides in surgery, with incisions preferentially running along the lines rather than cutting obliquely through them. This is because incisions along these lines heal with a minimum of scarring, whereas oblique wounds may be pulled apart or develop thicker scars. Collagen bundles that follow Langer's lines may interconnect over several millimeters, or even centimeters or more in extent. Some common directionality, at least on a local scale of a few hundred microns, is evident in the collagen structures in the skin of FIG. 2a. Collagen fibers generally do not often branch and, when branches are found, they usually diverge at an acute angle (see FIG. 1).

The natural mesh-like arrangement of collagen fibers in skin allows continual rearrangement of individual fibers to resist severe stretching under the minimal stresses associated with normal activity. At rest, the collagen fibers are irregularly organized, but when an increasing load is applied, the fibers change geometrical configuration and become parallel. The interconnected elastin fibers are able to stretch much more than the collagen fibers, and likely assist the collagen fibers to return to their original alignment after the forces have been removed. The water, proteins, and macromolecules (proteoglycans) function as lubricants during deformation.

Wounds are characterized in several ways; acute wounds are those that heal normally within a few weeks, while chronic wounds are those that linger for months or even years. Wounds that heal by primary union (or primary intention) are wounds that involve a clean incision with no loss of substance. The line of closure fills with clotted blood, and the wound heals within a few weeks. Wounds that heal by secondary union (or secondary intention) involve large tissue defects, with more inflammation and granulation. Granulation tissue is needed to close the defect, and is gradually transformed into stable scar tissue. Such wounds are large open wounds as can occur from trauma, burns, and pressure ulcers. While such a wound may require a prolonged healing time, it is not necessarily chronic. A chronic wound is a wound in which normal healing in not occurring, with progress stalled in one or more of the phases of healing. A variety of factors, including age, poor health and nutrition, diabetes, incontinence, immune deficiency problems, poor circulation, and infection can all cause a wound to become chronic. Typical chronic wounds are pressure, friction ulcers, and venous stasis ulcers. Chronic wounds often include necrotic tissue, which can comprise a mix of marginal cells, dead cells, and deteriorated extracellular structures. For example, marginal cells, which have impaired function, may also have cell morphologies (shape and size) that are different from those of normal cells. Likewise, with serious bacterial infections, excess levels of MMPs (matrix metallo-proteinases) such as gelatinase and collagenase, can cause extracellular supportive structures, such as collagen, to break down.

Presently, chronic wounds are categorized relative to the extent of the damage by the following stages:

Stage 1—has observable alteration of intact skin with changes occurring relative to skin temperature and color, tissue consistency and texture, and sensation (pain, itching). Pro-active treatment of Stage 1 and Pre-Stage 1 (also known as Stage 0) wounds could be beneficial.

Stage 2—involves partial thickness skin loss involving epidermis, dermis, or both. The ulcer is superficial and appears as an abrasion, blister, or shallow crater.

Stage 3—Full thickness skin loss with damage or necrosis of subcutaneous tissue.

Stage 4—Full thickness skin loss with extensive destruction, tissue necrosis, and damage to muscle, bone, or supporting structures (tendon, joint, capsule, etc.). Successful healing of Stage 4 wounds still involves a loss of function (muscles and tendons are not restored).

Stage 5—Surgical removal of necrotic tissue usually required, and sometimes amputation. Death usually occurs from sepsis.

Wound healing also progresses through a series of overlapping phases, starting with coagulation (haemostasis), inflammation, proliferation (which includes collagen synthesis, angiogenesis, epithelialization, granulation, and contraction), and remodeling. Haemostasis, or coagulation, is the process by which blood flow is stopped after the initial wounding, and results in a clot, comprising fibrin, fibronectin, and other components, which then act as a provisional matrix for the cellular migration involved in the later healing phases. Many of the processes of proliferation, such as epithelialization and angiogenesis (creation of new blood vessels) require the presence of the extracellular matrix (ECM) in order to be successful. Fibroblasts appear in the wound during that late inflammatory phase (~3 days post injury), when macrophages release cytokines and growth factors that recruit fibroblasts, keratinocytes and endothelial cells to repair the damaged tissues. The fibroblasts then begin to replace the provisional fibrin/fibronectin matrix with the new ECM. The ECM is largely constructed during the proliferative phase (~day 3 to ~2 weeks post injury) by the fibroblasts, which are cells that synthesize fibronectin and collagen. As granulation continues, other cell types, such as epithelial cells, mast cells, endothelial cells (involved in capillaries) migrate into the ECM as part of the healing process.

Fibroblasts initial role in wound healing is to provide fibronectin, which is a glycoprotein that promotes cellular adhesion and migration. Fibronectin weaves itself into thread-like fibrils, with "sticky" attachment sites for cell surfaces, to help connect the cells to one another. There is some directionality to the deposition of fibronectin, which in turn impacts the deposition of the other ECM proteins. Fibroblasts synthesize collagen (both Type I and Type III), beginning with procollagen, which is three polypeptide chains (each chain is over 1400 amino acids long) wound together in a tight triple helix. Procollagen is then extruded from the fibroblasts out into the extracellular space. Once exocytosed, these filaments lay disorganized in the wound, still in a gelatinous state. The triple-helical molecule undergoes cleavage at specific terminal sites. The helix is now called a tropocollagen molecule, and tropocollagens spontaneously associate in an overlapping array. The amassing continues as tropocollagen convolves with other tropocollagen molecules to form a collagen fibrin. Wound durability, or tensile strength, is dependent on the microscopic welding (cross-linking) that must occur within each filament and from one filament to another. The collagen fibril segments are ~25-50 microns in length and ~10-200 nm in diameter (depending on type). The fibril segments fuse linearly and laterally (crosslink) to form longer, thicker, biomechanically competent collagen fibrils within collagen bundles 145. Collagen deposition will align itself to the fibronectin pattern, which in turn mirrors the axis of the fibroblasts. Although the initial collagen deposition may appear somewhat haphazard, the individual collagen fibrils are subsequently reorganized, by cross-linking, into more regularly aligned bundles oriented along the lines of stress in the healing wound, and eventually, at least partially, to the stress lines associated with the surrounding tissue.

Type III collagen is the type that appears in the wound initially, starting at about 4 days after injury. Collagen becomes the foundation of the wound ECM, and if collagen formation does not occur, the wound will not heal. Myofibroblasts, which are a specialized fibroblast, appear late during the proliferative phase (at ~5 days), to help contract the wound so that there will be less scarring. Wound contraction helps to further organize the early collagen structures. A ring of these contractile fibroblasts convene near the wound perimeter, forming a "picture frame" that will move inward, decreasing the size of the wound. Linear wounds contract rapidly, square or rectangular wounds contract at a moderate pace, and circular wounds contract more slowly.

As wound healing progresses into the remodeling stage (starting at ~10 days post injury) the fibroblasts continue to work to build more robust tissue structures. Matrix synthesis and the remodeling phase are initiated concurrently with the development of granulation tissue and continue over prolonged periods of time (~30-300 days, depending on the injury). As the extracellular matrix matures, fibronectin and hyaluronan (a component of the proteoglycans) are broken down. Over time, fibronectin is replaced by Type III collagen and ultimately by Type I collagen. Type III collagen is fairly quickly replaced by Type I collagen, which constitutes 90% of the total collagen in the body, and forms the major collagen type found in the reticular dermis. As remodeling progresses, towards a goal of having the new ECM match the original and fit with the surrounding tissue, the collagen structure is altered on an ongoing basis, by a process of lysis and synthesis. Collagen degradation is achieved by specific MMPs (matrix metalloproteinases) that are produced by many cells at the wound site, including fibroblasts, granulocytes and macrophages. Gradually, the Type I collagen bundles are deposited with increasing organization, orientation, and size (including diameter), to better align to the surrounding tissues and increase wound tensile strength.

An ideal case of wound healing is one in which there is a complete regeneration of lost or damaged tissue and there is no scar left behind. In the case of a minor acute wound, which heals by primary intention, there will be little or no scarring, and the final tissue will be basically equivalent to the original. In the cases of an acute wound that heals by secondary intention (multiple layers of skin are injured), the healed wound will likely include some portion of scar tissue. Scars start as granulation tissue with large irregular mass of collagen. As with the primary union degree wound, scar remodeling for a secondary union type wound continues, attempting to mimic the surrounding tissue in structure and strength. The amount of scar to be remodeled is inversely related to the return of function. However, typically the fully healed scar has only 70-80% of the strength of the original tissue. In part this is because the collagen bundles never match fully match the original, nor regain the original alignments. Additionally, as adults produce few new elastin fibers during healing, the scar lacks the elasticity and recoil of the original tissue.

As previously stated there are several types of chronic wounds, including the pressure ulcer (or decubitis ulcers or bed sores), all of which suffer impaired healing. Stage 3 and Stage 4 pressure ulcers are open wounds that can occur whenever prolonged pressure is applied to thin skin and tissue layers covering bony prominences, such as at the hips and sacrum. For example, patients who are bedridden are at risk of developing pressure ulcers. Stage 4 pressure ulcers can form in 8 hours or less, but take months or years to heal. Pressure ulcers are complicated wounds, which can be large (many square inches in area) include infection, slough (dead loose yellow tissue), black eschar (dead blackened tissue with a hard crust), hyperkeratosis (a region of hard grayish tissue surrounding the wound), and undermining or tunneling (an area of tissue destruction extending under intact skin). Pressure ulcers may have closed wound edges (epibole), which impedes healing. In such circumstances, the top layers of the epidermis have rolled down to cover lower edge of epidermis, including the basement membrane, so that epithelial cells cannot migrate from wound edges. The efforts of the fibroblasts and the myofibroblasts to build the ECM and close the wound can be exhibited in a "collagen ridge" or "healing ridge," which is a region surrounding the wound (extending perhaps ~1 cm on each side) where new collagen synthesis is occurring. The collagen in healing pressure ulcer tissue is different than that in normal tissue, as there are fewer collagen fibers, but they may be significantly wider and longer than in normal tissue. FIG. 2b shows a scar-like mass of dense collagen fiber bundles from tissues near the boundary of a pressure ulcer.

As can now be appreciated, the biology of wounds and wound healing is complex, and diagnostic devices to assess the condition of the various related tissues (normal, necrotic, granulating, scar, etc.) would be useful. In considering the design of such devices, and particularly an optically based diagnostic device, there are several physical bio-markers which could be examined, including intra-cellular structures, cell morphology, and extra-cellular structures (such as the collagen networks and capillaries). Because of the size and complexity of chronic wounds, it would be useful to have diagnostic devices that could quickly examine "large" areas of tissue (for example, ~1 cm$^2$) and image "deep" (~2 mm+) into the tissues. Relative to optical imaging, both OCT and confocal approaches are relevant, because of their potential for depth imaging. More particularly, spatial light modulator based confocal and wide field of view OCT systems are attractive, because of the potential to quickly image an area with a compact device. However, in either case, there are opportunities to optimize these technologies for examination of wounds and the related tissues, by taking into consideration the physical and optical properties of these tissues.

To begin with, because dramatic changes in wound related tissues are significantly evidenced by macro changes in cell morphology and extra-cellular tissue structures, the resolution at the tissue need not be sub-cellular, and could be in the ~2-7 μm range. As a result, the numerical aperture (NA) of the objective lens is reduced, for example to ~0.2-0.3 from the ~0.7-1.4 values typical of OCT and confocal systems, thus simplifying the objective lens design (for example, thus obviating the need for immersion objectives). In turn, by reducing the lens NA, it is easier to provide a larger imaged field-of view, particularly when a modulator based architecture, similar to that of the Krause '832 patent is used.

Additionally, however, chronic wounds and the related tissues, have different optical properties than the normal dermal tissues. Thus, an optical diagnostic device, which is designed and used with recognition of these properties, is likely to provide more clinically useful data than an off the shelf system. Most optical tissue imaging systems are designed to operate within the spectral range of 600-1200 nm, where light attains its deepest penetration, because the light absorption coefficient ($\mu_a$) is relatively small (0.01-1 mm$^{-1}$). In this spectral regime, the interaction of light with tissue is dominated by scattering (the scattering coefficient $\mu_s$ is ~100× greater than the absorption coefficient $\mu_a$) where the total attenuation coefficient $\mu_T$ is given by equation (1).

$$\mu_T = \mu_a + \mu_s \sim \mu_s \quad (1)$$

Although cells and sub-cellular structures scatter light, it has been determined that dermal collagen is the dominant source of scattering in dermal tissues. As discussed in a paper by Kolarova et al., *Penetration of the Laser Light into the Skin in Vitro,* Lasers in Surgery and Medicine 24:231-235 (1999), the transmission of light in granulation tissue is ~2.5× higher than occurs in normal human skin. This then implies that the scattering coefficient in granulation tissue is significantly smaller than in normal tissue, and further that light will penetrate more deeply than in normal tissue.

As another consideration, in a paper by Nickell et al., *Anisotropy of light propagation in human skin,* Phys. Med. Biol. 45 (2000), pp. 2873-2886, it was shown that skin is optically anisotropic, such that the direction of minimal light scattering correlates with Langer's lines (see FIG. 2b). In particular, it was found that the scattering for light polarized parallel to the collagen fibers is different than scattering for light polarized perpendicular to the collagen fibers. Indeed, the perpendicular value is approximately equivalent to the reduced scattering coefficient $\mu_s'$ values generally quoted for skin, while the parallel value is ~2× smaller. An implication of this is that a polarization sensitive imaging system could, under the proper circumstances, probe more deeply than a polarization insensitive system. Further then, a polarization sensitive imaging system could then be used to look at collagen, and other optically birefringent structures, in skin. It is likely that part of the reason granulation tissue has higher optical transmission, is that the collagen network is less fully formed.

For example, in the case of suspected Stage 0/Stage 1 pressure ulcer tissues, a polarization sensitive imaging system could be used to look at collagen structures, or the lack thereof, in tissues, so as to determine the extent of damage. Likewise, such a device could be used to examine necrotic or semi-necrotic tissues, to help determine why the tissue is damaged, or where the tissue boundaries are. Finally, this device could be used to examine the condition of the rebuilding collagen in granulation tissues. More generally, it is recognized that successful collagen formation and remodeling is very important in wound healing, whether the wounds are acute (primary or secondary) or chronic, and whether the wounds are in the inflammatory phase, the proliferative phase, or the remodeling phase, or a combination thereof. In the case of chronic wounds, it could be valuable to have a device to detect the collagen structures in a Stage 3 or Stage 4 wound. It could also be valuable to have a collagen detection device that would facilitate detection of Stage 1 and Pre-Stage 1 wounds, by revealing semi-necrotic tissues and collagen structure degeneration. In that case, pre-emptive treatments could be attempted before the skin ruptures, which could greatly improve outcomes. Typically today, clinicians are not reimbursed for treatment of Stage 1 and Pre-Stage 1 conditions, as there are only subjective or visual measures available for tissue condition, rather than any quantitative measures.

It is noted that the diagnostic device of the present invention does not need to be limited to examining the collagen network, as a means for determining tissues status. Both elastin and fibronectin, which are elongated thread like proteins, are likely optically birefringent and could potentially be detected. As fibronectin is deposited prior to collagen Type I, detection of fibronectin could enable examination at an earlier point in the healing process. It is also noted that there are actually 14 different types of collagen. While collagens Types I and III are pre-dominant in the skin, the other collagens, which may also be optically birefringent, can be found in other biological structures. As an example, capillaries, which are tubules that are constructed in part with Type IV collagen, are known to be optically birefringent. Detection and tracking of capillary formation (angiogenesis) with the device of the present invention in tissue undergoing granulation and remodeling could also be useful in understanding tissue status. Additionally, muscles (which comprise a birefringent filamentous protein f-actin), nerves (which includes sheaths of birefringent myelin covering the axons), and amyloids (starch like birefringent proteins that aggregate and impair function, for example in Alzheimer's disease) might all be examined using the device of the present invention.

The possibility of examining birefringent tissue structures (collagen included) can then be a matter of providing polarization optics that can utilize the differences in light scattering, light transmission, and polarization orientation that occur as the light interacts with enable the optically birefringent structures. Isotropic (homogeneous) media (such as glass) have a single index of refraction, and are non-birefringent. Anisotropic media may have either two or three indices of refraction. Uniaxial media (such as liquid crystals) have two indices of refraction, which are the ordinary index ($n_o$) the extraordinary index ($n_e$). The axis of $n_e$ is also referred to as an optical axis. Uniaxial materials are uniquely characterized by $n_e$, $n_o$, and two angles describing the orientation of its optical axis.

Light sees varying effective indices of refraction depending on the polarization direction of its electric field when traveling through an anisotropic material, and consequentially, a phase difference is introduced between two eigenmodes of the electric field. This phase difference varies with the propagation direction of light, so the transmission of the light varies with angle when uniaxial or biaxial materials are placed between two crossed polarizers. It is generally understood that retardance is the delay of one polarization relative to the orthogonal polarization, where the delay translates into a phase change $\Delta\phi$ in the polarization of the incoming light. The phase change $\Delta\phi$ can be calculated as $$\Delta\phi = 2\pi * t * \Delta n / \lambda, \qquad (2)$$

where ($\Delta n$) is the index change ($\Delta n = n_\| - n_\perp = n_e - n_o$) (intrinsic birefringence) provided by the structure and (t) is the thickness of the structure. Retardance is the phase change $\Delta\phi$ expressed as distance; for example a $\pi/2$ phase change $\Delta\phi$ corresponds to a quarter wave $\lambda/4$ retardance, which at 550 nm equals ~138 nm retardance. These phase differences translate into modifications of the local polarization orientations for rays traveling along paths other than along or parallel to the optical axis. When viewed under polarized light, however, anisotropic materials will be brightly visible in one plane ("birefringent"), but will be dark in a plane turned 90 degrees. The refractive index of human tissue (collagen included) is n~1.4-1.5, depending on the tissue and the wavelength. Both Type I and Type III collagens are birefringent, with nominal optical birefringence values of $\Delta n \sim 3 \times 10^{-3}$.

The present invention then provides a diagnostic imaging device for examining dermal tissues, and specifically wounds and the associated tissues, with specific consideration given to the physical and optical properties of these tissues. A basic device concept was described in commonly-assigned copending U.S. patent application Ser. No. 11/087,183, as shown in FIG. 3. A tissue imaging system 200 comprises an illumination system 205 and a detection system 210 (linked by a controller (not shown) and a beamsplitter 260), which are both directed at the same nominal portion of tissue 290. Note that FIG. 3 is not to scale; the optical systems likely measure several inches end to end, but the depth of the tissue examined is only ~2-4 mm. In the conceptual device of FIG. 3, both the illumination system 205 and the detection system 210 are aimed obliquely at the tissue 290. The illumination system 205 nominally comprises a light source and illumination beam shaping optics. Light source can be a lamp (such as tungsten halogen, metal halide, or UHP), an LED (light emitting diode), a SLD (super-luminescent diode), a laser diode, a solid state laser, or other light source, such as an array with multiple light emitters 225. The beam-shaping optics can comprise a condenser lens 230, a pre-polarizer 250, spectral filters (not shown), light uniformization optics, and field lenses (such as field lens 240), as well as other components.

Optical detection system 210 nominally comprises an objective lens 270 that provides an image of the tissue 290 on detector 280. Detector 280 is nominally a detector array, such as a charge coupled device (CCD) or a complementary metal oxide semiconductor (CMOS) device. Detector 280 is nominally an area sensor device with a row and column structure. An exemplary device could be the Kodak KAF-6303, which comprises an array of 3072×2048 pixels, with a nominal 9 micron pixel pitch. Incident light provided by the illumination system 205 will penetrate the tissue 290. Some portion of this incident light will be reflected or backscattered from the various tissue components (organelles, cells, and extra-cellular components such as collagen) it encounters and can be imaged by objective lens 270 onto detector 280. Tissue imaging system 200 is nominally equipped with at least two linear optical polarizers, pre-polarizer 250 and polarization analyzer 255 that are provided to enable detection of the birefringent tissue structures. Either pre-polarizer 250 or a waveplate 252 rotates around the illumination optical axis 247, while polarization analyzer 255 rotates about the imaging optical axis 277. These two polarizers are nominally orthogonal to their respective axes, although they may be tilted (likely by a few degrees) away from orthogonality, to control the direction of any ghost reflections, to thereby improve image contrast. Additionally, pre-polarizer 250 and polarization analyzer 255 are nominally crossed (90 degrees rotationally apart) to define extinction axes. Light from the illumination system 205 is then incident on the tissue 290 with an initial linear polarization alignment. Some of this light will penetrate the tissue 290, and another portion will be specularly reflected from the first surfaces (the superficial layers: the epidermis 105 and papillary dermis) of the tissue. This specularly reflected light tends to retain the polarization state of the illumination light. Light that penetrated tissue 290 and then re-emerges while nominally retaining the initial polarization state will be eliminated by crossed polarization analyzer 255 and not reach detector 280, and therefore not provide an effective image. Likewise, the polarization analyzer 255 will also eliminate the specularly reflected light from the first surface of the tissue. Whereas, light that re-emerges from tissue 290 with its polarization rotated to some extent by the birefringent structures within the tissue, can then have some portion of that light transmitted through polarization analyzer 255, imaging field lens 275, and thus imaged at detector 280. Re-emergent light that has a polarization vector orthogonal to the illumination polarization axis, and therefore nominally aligned to the polarization axis of the analyzer 255 will be imaged with maximal image brightness.

In this way, the polarization sensitive optics enable the imaging of the birefringent tissue structures by enabling detection of changes in the polarization state of the low level diffused light re-emerging from the tissue, while eliminating the strong initial back reflection off of the front surface, which could otherwise provide a dominant return signal and reduce the contrast of the images of the birefringent tissue structures.

Recall that the collagen network in relaxed skin likely has local directional variations (see FIGS. 2a and 2b), thus the birefringence is spatially variant. Therefore, the image quality of the collagen network depends on the relative alignment of the crossed polarizers (250 and 255) to any given portion of the network. Thus to improve the quality of the images of the collagen network, the concept of the FIG. 3 system anticipates that the crossed polarizers should be rotated in unison so that the extinction axes rotate into various positions relative to the tissue 290. This is facilitated by controller, which sends drive signals to mechanisms (not shown), such as stepper motors, which separately drive pre-polarizer 250 and polarization analyzer 255 to rotate about their respective optical axes. Nominally crossed polarizers 250 and 255 each rotate by the same angular amount $\Delta\theta$, so that they remain crossed. Crossed polarizers 250 and 255 nominally are rotated in a stepwise fashion through N steps, of some set amount Δθ, until the crossed polarizers have both swept through at least 90 degrees. At each step, the controller would drive the light source to provide illumination light and detector 280 to capture a digital image. The controller could employ image-processing algorithms to build one or more composite high contrast images. These image-processing algorithms could perform various functions (sharpening, contrast changes, false color, etc.) to enhance image quality/wound visualization. It was further proposed that this device could be used in a therapeutic mode, using illumination system 205, to provide light for light therapy.

In this prior commonly-assigned copending application, it was suggested that a multi-spectral imaging approach could be used to see structures at different depths. For example, the light source (using spectral filters or different sources) could sequentially provide illumination light with an increasing nominal wavelength, starting at ~530 nm (to image structures within the first ~0.5 mm tissue depth), then ~600 nm (to image structures within the first ~1 mm tissue depth), then ~630 nm (to image within the first ~2 mm tissue depth), and ~830 nm light (to image within the first ~3.5 mm tissue depth). Then for each rotational position of the crossed polarizers 250 and 255, the controller could capture digital images for each tissue depth. It was then suggested that the controller could apply a form of spectral polarization difference imaging, such that data for shallower images was subtracted from the original data for deeper images, to remove scatter and birefringence effects caused by the shallower images. While this approach may work for some tissue types, perhaps including granulation tissues, for tissues such as skin (particularly the dermis 120), which are affected by strong optical scattering, the effectiveness may be limited when attempting to image deeper and deeper into the tissues.

Figure 4A:
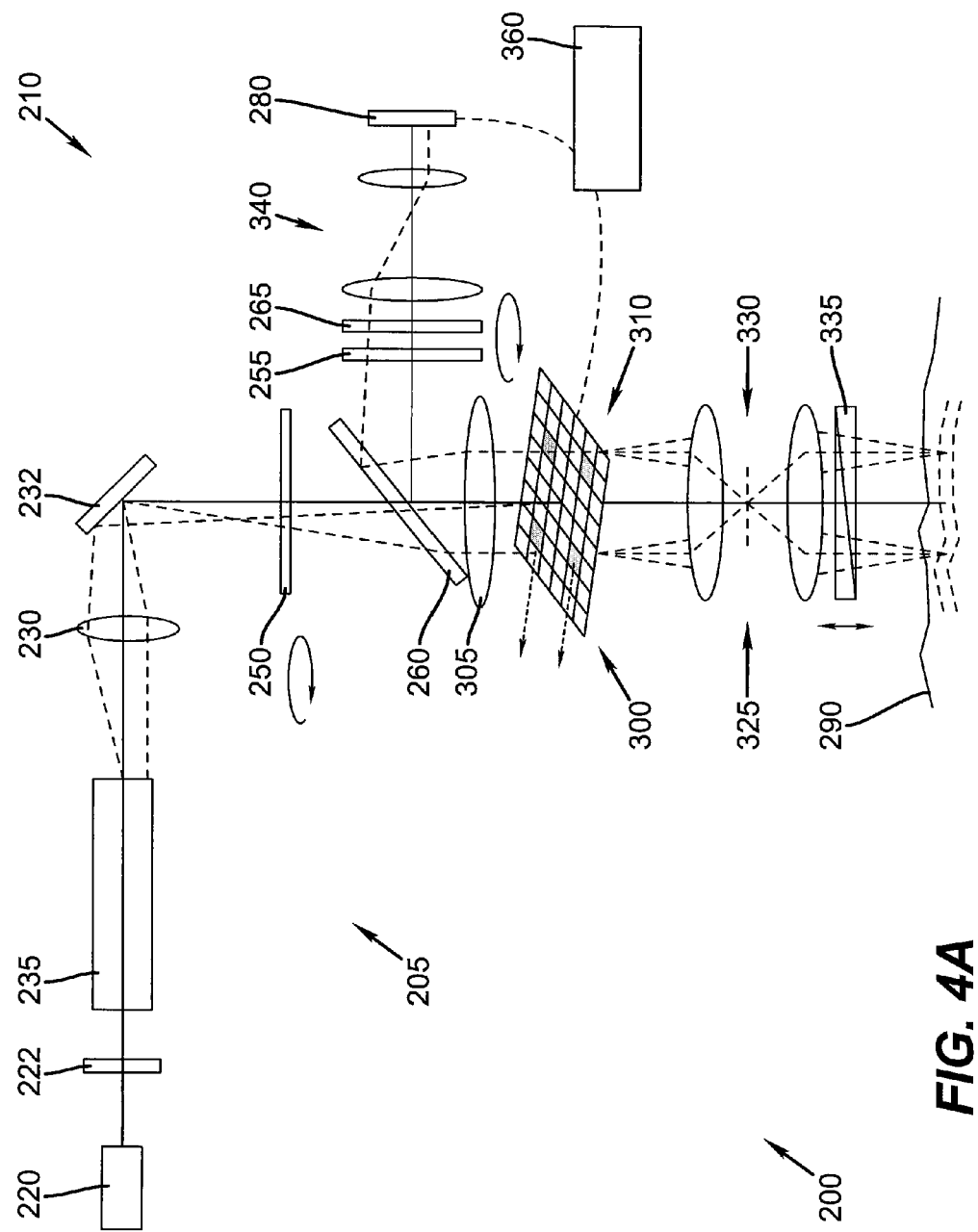
FIG. 4a is a view of the first embodiment for a programmable confocal tissue imaging system of the present invention.

In order to provide improved depth imaging capability compared to the system of FIG. 3, alternate concepts for optical imaging diagnostic devices have been developed. As a first example of a tissue imaging system 200 of the present invention, FIG. 4a depicts a system that includes a spatial light modulator array 300, which is nominally image conjugate to both the tissue 290 and the detector 280. FIG. 4a is a conceptual illustration, with most components shown in cross-section, except for spatial light modulator array 300, which is shown in perspective. The components of the system of FIG. 4a are not shown to scale. In this system, a light source 220 is used to illuminate the spatial light modulator array 300, via exemplary illumination optics which comprise a diffuser 222, an integrating bar 235, a condenser lens 230, fold mirror 232, and beamsplitter 260. This illumination system, which is intended to flood illuminate the entire top surface of spatial light modulator array 300, should provide improved illumination uniformity as compared to other classical approaches (such as Kohler and Abbe illumination). For example, light from light source 220 may be directed to (optional) diffuser 222, which diffuses the light into integrating bar 235. The output face of integrating bar 235 is then imaged to the modulator array 235, to flood the surface with uniform (nominally within a few %) light. As one alternative, an illumination system with a Fly's Eye optical integrator can also be used to provide enhanced illumination uniformity. Modulator field lens 305 can be used to modify the incident illumination light to be telecentric to the spatial light modulator array 300. Objective lens 325 then images the modulator array 300 into the tissue 290, and then collects return light from the tissue 290, which it images back to the spatial light modulator array 300. Modulator 300, objective lens 325, and focus mechanism 335 can also be defined as the scan arm of tissue imaging system 200. Imaging lens 340, in cooperation with modulator field lens 305, then images modulator array 300 to the detector array 280. The system can also be equipped with a pre-polarizer 250 and a polarization analyzer 255. As compared to the prior system of FIG. 3, this system is enhanced primarily by the use of spatial light modulator array 300, and the change of the objective lens to a doubly-telecentric (nominally telecentric in both object and image spaces) design.

The tissue imaging system of FIG. 4a is primarily intended to operate as a flexible confocal imaging system, with the confocal imaging modality enabled by modulator array 300, which functions as a programmable pinhole. In FIG. 4a, modulator array 300 is depicted with 4 addressed modulator pixels 310 "shaded," to indicate that they are simultaneously "open" to allow light down to the tissue and back. As shown in FIG. 4a, spatial light modulator array 300 is preferably a transmissive device, because the overall size of the tissue imaging system 200 is likely then reduced. One exemplary device is the "flixel" from Flixel Ltd. of Tel Aviv, Israel, which comprises an array of flipping "door-like" panels, and which is described in prior art patent U.S. Pat. No. 6,600,474 (Heines et al.). Another exemplary device, which is also a microelectromechanical (MEMS) device, is the coiled or rolled shutter modulator, which is described in U.S. Pat. No. 5,784,189 (Bozler et al.). Both of these devices function by moving a micro-mechanical shutter, which blocks the light when closed, but which is moved out-of-the-way, to provide open state transmission. As a result of their structural simplicity, these devices are advantaged in that the phase structure of the passing light beams is less likely to be altered in transit, and therefore, the effective resolution of the light imaged to the detector 280 may be better. Another candidate modulator technology is the polymer dispersed type liquid crystal display (LCD). It modulates light by causing the transiting light to scatter within an off-state pixel, while having high transmission and low scatter for an on-state (field applied) pixel. However, such a device could impart residual phase distortions to the transiting image light or require a Schlieren type stop, located for example at aperture stop 330, to filter out the off-state light from the on-state light.

In more detail, when a modulator pixel 310 is open (or on-state), illumination light would travel through objective lens 325 and illuminate small portions of a sample or specimen, such as tissue 290. Return light from tissue 290 would be spatially filtered by the same pixel at modulator array 300. This light would then deflect off beamsplitter 260 and be imaged by imaging lens 340 to detector 280, which may be a CCD device, a CMOS, or other type of detector array. A given modulator pixel 310 would then provide the functionality of a pinhole in a confocal microscope. After given pinhole image captures, controller 360 would then provide signals to modulator array 300 to change the combination of open pinholes to a new configuration. Over time, a series of pinhole image captures would be completed such that a complete confocal image could be completed at a given plane within tissue 290. Then the focal position within the tissue could be changed, for example, through the use of focus mechanism 335 (shown as a wedge prism pair, which are adjusted laterally relative to one another, to alter the optical path length) under the control of controller 360. A complete confocal image could then be captured at the new plane within the tissue. Ultimately, by a sequence of re-focusing and confocal image capture, a complete 3D image could be obtained, spanning a given tissue area and depth.

In order to optimally capture confocal images using a modulator array 300, it is best that a doubly-telecentric objective lens 325 be used, so that the illumination light and the return light travel through the same modulator pixel (pinhole). By comparison, with a non-telecentric objective lens 325, in which the chief rays are not nominally normally incident to the target plane, the light returning to the modulator site is likewise exiting non-normally to the target (tissue). As a result, the angles of incidence and collection will vary over the target plane. As area images are re-assembled at different depths, this could cause parallax and distortion image errors. Additionally, with telecentric imaging, the system could benefit from less aberration (field curvature) and higher light collection efficiency and uniformity from the tissue. However, the refocusing of a double telecentric imaging lens 325 to alternate conjugate image planes is different than occurs with a normal imaging lens, as the chief ray heights are fixed. Such refocusing can then cause both a magnification change and vignetting at the aperture stop. As an alternative, the system of FIG. 4a is depicted with a wedge plate focus mechanism 335 being used on the tissue (short conjugate) side of the lens. As the two wedge plates are moved (slid) relative to each other, the effective glass thickness is changed, and thus the optical path length and focal position within the tissue is changed, and yet the magnification is held constant and vignetting is avoided. The target focus plane within tissue 290 can then be adjusted to different axial locations within the tissue.

As an example, tissue imaging system 200 could utilize a modulator array 300 comprising pixels 310 that are 17 microns square. If the objective lens 325 images to the tissue with 4.25:1 de-magnification and a short conjugate NA of ~0.25, then the geometrical size of the imaged "pinhole" in the tissue is $d_g$~4.0 microns. An exemplary objective lens 325, as shown in FIG. 4b, does not require exotic glasses or unusually difficult lens elements. A reflective design could also be used, but should not be necessary, given the limited source bandwidth and small target NA at the tissue. This exemplary lens is designed to image with a ~1 inch working distance between the last element and the target plane. An exemplary modulator array 300 with a ~1.95 inch diagonal and ~4 Mpixels is then imaged to the tissue to address an area of ~0.7 cm^2, which should be large enough for useful diagnostic application. A confocal term, the virtual pinhole diameter Vp at the target plane, which can be estimated by equation (3), is a metric that can be used to anticipate the confocal optical imaging depth and confocal resolution in the tissue. The imaging depth ($D_Z$) is scalable with the mean free path, which is the inverse of the total attenuation coefficient $\mu_T$, with the scaling factor (A) depending on the value of the virtual pinhole diameter Vp. The confocal lateral resolution dr, which is different than the geometrical size of the imaged pinhole, is scalable to the minimum confocal resolution $r_{conf}$ by a factor (B), which is determined by the value of Vp.

$$V_p = \pi * d_g * NA/\lambda \qquad (3)$$

$$D_Z(V_p) \sim A*mfp \sim A/\mu_T \qquad (4)$$

$$dr(Vp) = B*r_{conf} = B*0.88*\lambda/(n*NA) \qquad (5)$$

As the value of virtual pinhole diameter Vp approaches one, lateral and axial resolution, imaging depth, and signal to noise ratio are all maximized, but at the cost of decreased optical signal strength. Using the above parameters, a virtual pinhole diameter Vp~3.9 is estimated for a wavelength of 810 nm. When imaging in normal skin tissues, which have a large scattering coefficient $\mu_p$~13 mm$^{-1}$, the imaging depth $D_Z$ for this system can be estimated by the equation (4) as 0.2-0.35 mm. However, as the previously noted large increase in the light transmission of granulation tissue (relative to normal skin tissue) implies a dramatic reduction in light scattering, then the imaging depth in granulation tissue can be expected to improve accordingly. Using then an estimated granulation tissue scattering coefficient $\mu_s$~1.8 mm$^{-1}$, an estimated confocal imaging depth $D_Z$~1.7-2.6 mm is obtained. Thus, it can be anticipated that a confocal imaging system could potentially image a few mm into granulation tissues, and perhaps other wound tissues such as necrotic and semi-necrotic tissues. The estimated lateral resolution, dr ~4 microns, should be sufficiently small to image both extra-cellular tissue structures and the morphology of many cell types to be useful in examining wound tissues.

This first FIG. 4a embodiment of the present invention can have other attributes and features that enhance its utility. For example, it is noted that the system of FIG. 4a, like the prior system of FIG. 3, may also have dual diagnostic and therapeutic use. Most simply, if all the modulator pixels 310 are controlled to an open state, then the tissue 290 could be flood illuminated with light for therapeutic purposes. Likewise, if all the modulator pixels 310 were at an open-state, and the detector array 280 was operated for image capture, then system 200 could operate as a digital camera or microscope and capture photographic images of the tissue 290.

The tissue imaging system 200 can have other attributes and functions beyond operation as a camera or light therapy device. As one possibility, consider that as a wound heals and granulation tissue becomes more like normal skin tissue or scar tissue, the scattering would likely increase and the imaging depth would then be diminished. On the other hand, as reported in the previously cited paper by Nickell et al., skin has a polarization anisotropy based on collagen orientation, such that light polarized parallel to the collagen orientation experiences a reduced scattering coefficient ~2x smaller than normal. This suggests that a polarization sensitive confocal-type imaging system could collect this parallel-polarized light, and thus enable deeper imaging within some tissues. As an example, then applying an estimated collagen parallel scattering coefficient $\mu s$~4.9 mm$^{-1}$, a confocal imaging depth of $D_Z$~0.7-1.0 mm is predicted.

To facilitate this polarization sensitive imaging, the tissue imaging system 200 of FIG. 4a, in like fashion to the system of FIG. 3, can be equipped with optical polarizers, such as pre-polarizer 250 and polarization analyzer 255. Preferably, polarization analyzer 255 is stepwise rotated by controller 360 through various angular positions from 0-90°, so that the light parallel polarized to the collagen at a given tissue depth, but at various combinations of location and orientation within the field of view, can then be imaged. As with the description of the system of FIG. 3, the pre-polarizer 250 in FIG. 4a can be held in a position which is nominally orthogonal or crossed with respect to polarization analyzer 255, and then be stepwise rotated in synchronization with polarization analyzer 255. In this way, specular surface reflections from the first surface of the tissue can be minimized. There are several other approaches however for handling the polarization light capture in order to maximize tissue structure visibility. As on example, for each rotational position of the pre-polarizer 250, the polarization analyzer 255 can be driven to both parallel and orthogonal positions, with image captures then occurring. A polarization difference image, with the polarization parallel image subtracted from the polarization perpendicular image (and normalized by the sum of the two) could then be compiled, so as to emphasize the deeply penetrating light. However, for injuries such as acute and chronic wounds, in which the superficial (epidermal) skin layers are often removed, a strong "first" surface polarized reflection may be absent. As a result the pre-polarizer 250 and polarization analyzer 255 could be aligned parallel (rather than crossed, and then rotated in tandem by controller 360. As another approach, a linear pre-polarizer 250 could be followed by a waveplate to produce circularly polarized illumination light. The return light would tend to be circularly polarized, and polarization analyzer 255 could be rotated to various positions to detect the aligned image information. Alternately, pre-polarizer 250 may be removed altogether, but that could result in an increase in the noise level from stray light reaching the detector 280.

The choice of polarization optics used in the polarization diagnostic device of the present invention can be important. Many prior art optical systems have been described which use MacNeille type thin film prisms (U.S. Pat. No. 2,403,731), pulled polymer sheet polarizers ("Polaroid" polarizers), or bulk birefringent crystalline prisms (such as calcite). In recent years, visible wavelength wire grid polarizers have been developed. These polarizers, which are available from Moxtek (Orem, Utah), and which are described in U.S. Pat. No. 6,122,103 (Perkins et al.) and U.S. Pat. No. 6,243,199 (Hansen et al.), have many admirable features, including a broad spectral response, a broad angular response, high contrast, and good transmission (~90%). In the main, these inexpensive devices are being used for image projection systems with liquid crystal displays (LCDs), where it is important to obtain high polarization contrast as well as good transmission with a fast (~F/2.4) optical system. Exemplary systems and wire grid devices have been described, for example in U.S. Pat. No. 6,532,111 (Kurtz et al.), U.S. Pat. No. 6,585,378 (Kurtz et al.), and U.S. Pat. No. 6,909,473 (Mi et al.) (all originally assigned to the same assignee as the present invention) in which wire grid polarizers were applied in projection systems intended to provide projected contrast of >1000:1. Indeed, operational systems have been described in the literature, in which projected image contrast levels >4000:1 have been reported. High polarization extinction could be useful in detecting weak polarization signals from the weakly birefringent tissue structures.

Figure 4C:
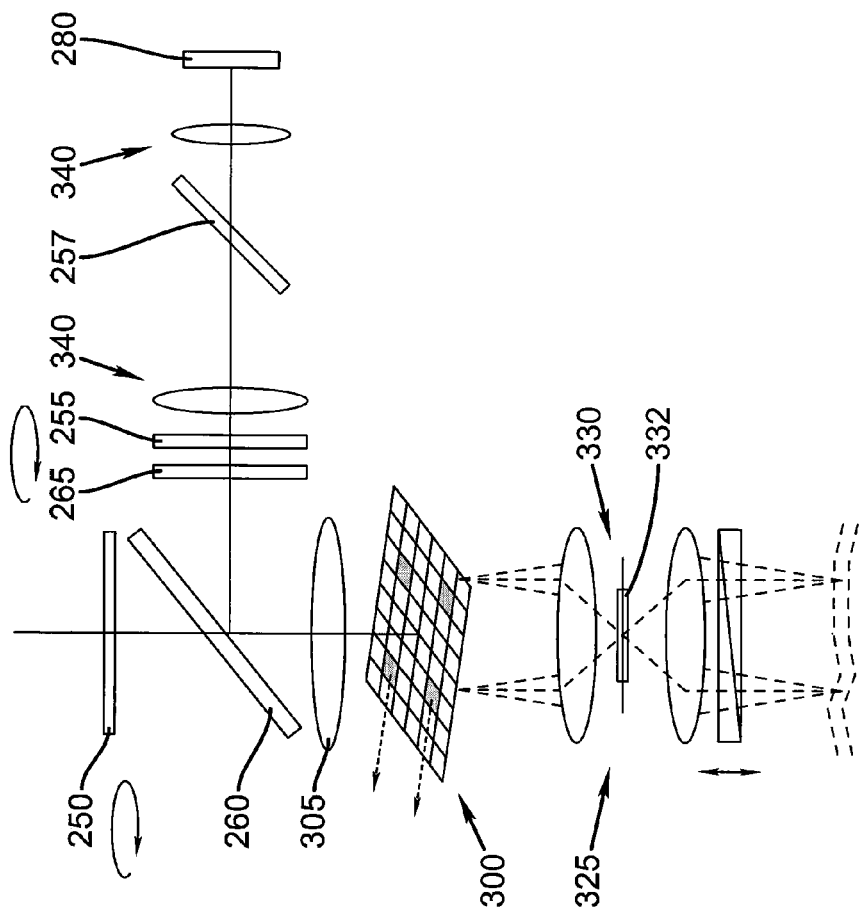
FIG. 4c is a view of an alternate embodiment of an imaging sub-system for a tissue imaging system of the present invention.

Relative to the tissue imaging system 200 of FIG. 4a, it should be understood that both pre-polarizer 250 and polarization analyzer 255 are preferentially wire grid polarizers. Of course, several variations on the theme are possible. For example, polarization analyzer 255 might actually be two consecutive wire grid polarizers, with the second one provided to remove residual leakage light from the first, and thus enhance the contrast. In that case, both polarizers would rotate together as a pair, although the two polarizers might be tilted relative (by a few degrees, or near parallel) to each other to control ghost reflections. Alternately, as shown in FIG. 4c, a polarization analysis subsystem could be utilized, with a waveplate 265, a polarization analyzer 255 (preferably a wire grid polarizer) and a wire grid polarization beamsplitter 257 (the latter is a wire grid polarizer nominally tilted at 45 degrees relative to the optical axis of detection system 210, and performance optimized for the tilt). Preferentially, the incoming image light returning from the tissue would be transmitted through the waveplate 265, the polarization analyzer 255 and the wire grid polarization beamsplitter 257, before reaching detector 280. In this case, the two polarizers would maintain a fixed polarization parallel position, and the waveplate (¼ wave) would rotate the polarization orientation of the incoming light relative to the paired polarizers. In this configuration, residual light of the wrong polarization would be reflected out of the imaging system by wire grid polarization beamsplitter 257, thereby improving image contrast. Equivalently, waveplate 265 could also be an electro-optical device, such as liquid crystal device, which would provide an amount or polarization rotation in response to a commanded signal. In this way, the use of rotating mechanical part could be avoided and the capture time is reduced. The polarization contrast of this system could further enhanced with the use of a polarization compensator (not shown), for example, located prior to wire grid polarization beamsplitter 257. This compensator could correct for angular response variations of the beamsplitter 257.

The polarization design of the illumination system 205 is also worth further consideration. In the circumstance that light source 220 emits polarized light (for example if it comprises one or more laser diodes, then pre-polarizer 250 could be replaced with a waveplate (nominally $\lambda/4$) which would rotate the polarization state of the incident light relative to tissue 290. However, if the light source 220 emits unpolarized light, it could be disadvantageous to build the illumination system 205 with a pre-polarizer without first (or instead) providing a polarization conversion device, as otherwise as much as 50% of the available light will be lost right up front. While there are many polarization conversion designs known in the art, one particularly advantageous design and compact is described in U.S. Pat. No. 5,978,136 (Ogawa et al.), which uses an array of mini-prisms and waveplates to provide an ensemble of polarized light beams. In that case, pre-polarizer 250 could comprise a rotating polarization converter, or a fixed polarization converter and a rotating waveplate. Certainly other polarizer technologies with high contrast and transmittance, as well as a large angular acceptance, could be used in place of wire grid polarizers. For example, another candidate technology is the photonic crystal polarizer, which theoretically has an excellent field-of-view and wavelength acceptance. Such devices are available from Photonic Lattice Inc. (Japan). However, photonic crystal polarizers are presently fabricated using expensive lithographic processes.

The potential utility of the tissue imaging system 200 can also be enhanced or expanded relative to the light source 220. In general, it is assumed that light source 220 is illuminating with a spectra residing within a spectral window from ~500 nm to ~1200 nm. Depending on whether light source 220 is a lamp, an LED, a super-luminescent diode (SLD), or a laser diode (or multiples or combinations thereof), the illuminating spectra may be broad (40 nm or greater) or quite narrow (1-4 nm). Multiple light sources with different emission spectra may also be used. The illumination light can then scatter off of tissue structures in the target plane, with some portion thereof imaged back to the modulator array 300 and onto the detector 280. Alternately, the illumination light could excite fluorescent emissions within the tissue, and fluorescent light could be imaged. As one example, when collagen is illuminated with ~400 nm light, it produces a strong fluorescence at ~480 nm. The detection of the fluorescent light could be enhanced by providing one or more filters in the detection system 210, which could be either fixed spectral filters or tunable spectral filters (such as a liquid crystal tunable filter). In particular, as it has been shown that collagen fluorescence is reduced as a byproduct of the action of MMPs (such as collagenase) to degrade collagen, as can happen in wounds, then imaging collagen fluorescent light could be useful in wound assessment to look at tissue deterioration. Unfortunately, collagen fluorescence from the longer illumination wavelengths (>600 nm) necessary for deep tissue penetration is much reduced. Conceivably, other fluorescence techniques, such as second harmonic generation and multi-photon excitation could be used, but as the requisite light sources are typically expensive high power femto-second pulsed lasers, use thereof in tissue imaging system 200 would likely cause the system to exceed the size and cost targets desired for this application.

As another aspect, beamsplitter 260 can be designed using any one of several technologies. Generally speaking, either the detection channel light (as in FIG. 3) or the illumination light (as in FIG. 4*a*) can be transmitted through the beamsplitter (relative to the tissues 290). Beamsplitter 260, for example, can most simply be an intensity splitter (prism/cube or plate), that for example, transmits 60% of incident light and reflects 40% of incident light. Alternately, beamsplitter 260 can be an angle sensitive TIR prism, much as depicted in FIG. 3, which comprises two transparent prisms having angled surfaces internal to the overall prism, such that the internal surfaces are substantially parallel to each other and the gap is filled with a low refractive index material (such as air or a low index optical adhesive). The combination of the angular orientation of the internal angled surface of the first constituent prism and the refractive index of this first prism is such that the illumination light incident thereupon is reflected (at greater than the critical angle) towards tissue 290 by total internal reflection (TIR). Both the intensity splitter and the TIR prism have the advantage that they are polarization insensitive devices, which makes them particularly useful for a tissue imaging system 200 with an illumination system 205 in which the illumination light is provided with a variably rotating polarization orientation. Alternately, if the system 200 was designed specifically to utilize fluorescence, then beamsplitter 260 could be a dichroic, which would selectively reflect and transmit light on the basis of wavelength (excitation or emission). If there were multiple fluorescent emission wavelengths that needed to be distinguished, a Color Select filter or a Color Switch filter from ColorLink of Boulder, Colo., could be used in the detection channel, to selectively rotate the polarization states of one wavelength and not another. A polarizer could then follow, which would attenuate one wavelength and allow the other through to the detector 280. The configuration could be similar to that of FIG. 4*c*, where waveplate 265 could be a wavelength selective polarization switch. Alternately, if a tissue imaging system 200 is constructed with fixed orthogonal polarization orientations for the illumination and detection channels, then beamsplitter 260 could be a polarization beamsplitter (such as a wire grid PBS or a MacNeille type PBS) that transmits one polarization state, while reflecting the other. For the present invention, which nominally is designed with rotationally variable polarization to enable viewing of spatially variant polarization structures, this could mean that the entire tissue imaging system 200 would then have to be rotated relative to tissue 290.

FIG. 4*c* also shows that the tissue imaging system could be equipped with a pupil filter 332, nominally located in the aperture stop plane 330 of objective lens 325. "Pupil filter" 332 could be used to help control or define the axial resolution of the system. Pupil filter 332 could have an annular design or a central obscuration, providing a zonal pattern that modifies the intensity (apodizing) and/or phase of the transiting light. The use of a pupil filter 332 may also improve the signal to noise ratio of the imaging light. A Fourier plane filter (not shown) could also be used at the aperture stop of the imaging lens 340, for various purposes, including to filter out the periodic structure signatures of the spatial light modulator array 300.

Figure 4D:
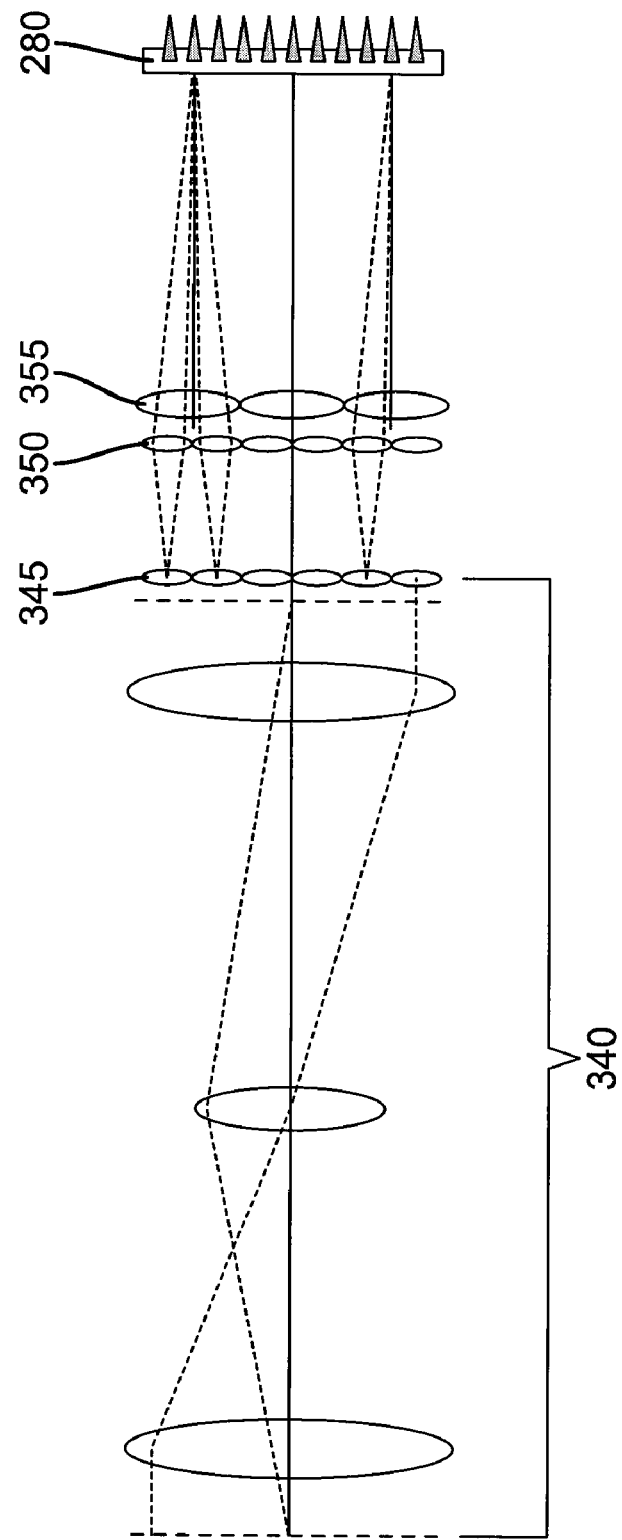
FIG. 4d is a cross sectional view of an alternate embodiment of an imaging sub-system within a tissue imaging system of the present invention.

As another consideration, in the prior discussions, an exemplary system was described in which spatial light modulator array 300 was a device with 4 Mpixels, or ~4 million addressed "pinholes." In collecting the tissue images, for improved spatial resolution, it may be desirable the detector array 280 to be provided with more detection pixels than there are modulator pixels. For example, with a ratio of 4×, detector array 280 would then have 16 Mpixels. While image sensors are available today with 14 Mpixels or more, data handling, data storage, image processing, and signal to noise ratios may all be affected by increasing the pixel count of the detector array 280. As an alternative, FIG. 4*d* depicts an approach for optically multiplexing the detector pixels. In this exemplary case, imaging lens 340 would project or create an intermediate real image, which is image conjugate to spatial light modulator array 300. That image would then be optically sub-sampled by an optical system comprising first lenslet array 345, second lenslet array 350, and field lenslet array 355. Second lenslet array 350 and field lenslet array 355 would work together to project a magnified image to detector array 280. First and second lenslet arrays 345 and 350 would be paired, so that first lenslet array 345 would act as a field lens relative to the input image plane, and nominally focus light into the aperture stop of the corresponding lenslet of second lenslet array 350. As shown, field lenslet array 355 would receive light from multiple 345/350 lenslet pairs. As a result, the images from a first 345/350 pair and a second 345/350 belonging to a given lenslet of field lenslet array 355 would fall onto or overlap the same pixels of detector array 280. But the images from 345/350 lenslet pairs belonging to a given lenslet of field lenslet array 355 do not overlap the images cast by 345/350 lenslet pairs corresponding to another lenslet of field lenslet array 355. The addressing of spatial light modulator array 300 would be controlled to avoid a simultaneous overlap of images of different modulator pixels at detector array 280. However, the number of lenslets in field lenslet array 355 would need to be large enough to make the simultaneous addressing of spatial light modulator array 300 time efficient. Care would be needed in the optical design to ensure that optical image quality was not significantly degraded by employing this optical sampling and re-imaging approach. For example, the lenslets could be designed with refractive aspherical curvature profiles or diffractive optics features, as degrees of freedom to improve image quality. The system of FIG. 4*d* is representative, and other designs using alternate lenslet array configurations are possible. Obviously, this approach would impose a burden on the image processing.

Figure 4E:
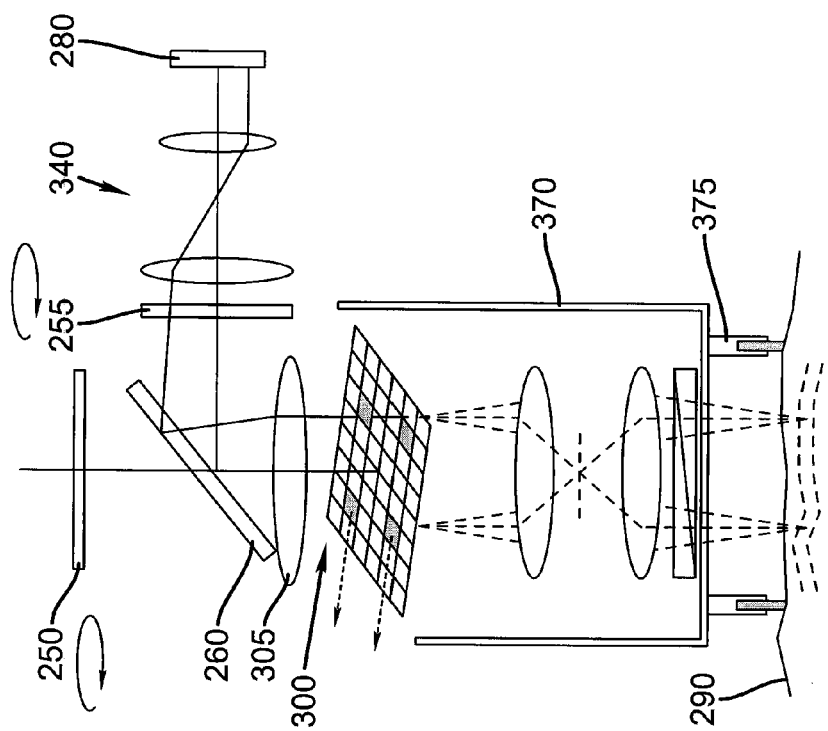
FIG. 4e is a view of an alternate embodiment for a tissue imaging system of the present invention to have a controlled interaction with the tissue being examined.

This system may also need to be equipped with some supports 375, attached to a surrounding housing 370, as shown in FIG. 4*e*. These supports could be used to help hold tissue imaging system 200 in a mechanically stable position during image capture. Supports 375 could also be adjustable relative to the tissue 290, to provide a focus control in addition to, or in instead of focus mechanism 335. Focus mechanism 335 has been generally described as employing an opposing wedged plate construction, but other technologies, such as electro-optical devices, could be used instead. Care will be needed in the design of focus mechanism 335 to avoid strong back reflections that could overwhelm the intended signals. A transparent top sheet (not shown) may also be used between the tissue imaging system 200 and the tissue 290 to limit cross-contamination. In the case that objective lens 325 is non-telecentric, the focus means could be provided with a moving lens or lens group within said lens 325. It is also noted that the light source 220 could be pulsed or modulated as a synchronization means to compensate for instability of the tissue imaging system 200 relative to the tissue 290.

The signal to noise ratio for tissue imaging system 200 is impacted by the pinhole size and the rejection of out of focus backscattered light, tissue type (scattering coefficients), the optical design, and the detector properties (such as shot noise, gain, and bandwidth). As an example, the optical rejection of alternate polarization state light by polarization analyzer 255 may have a significant impact on the signal detection and imaging. In reconsidering the system 200 of FIG. 4*a*, there are opportunities to improve the design so that the optical noise is reduced and signal detection is then improved. In particular, as was previously described, the illumination system 205 provides flood illumination to spatial light modulator array 300. In the case that the significant off state light is retro-reflected from the top surface of spatial light modulator array 300, then significant amounts of this reflected light could in turn be reflected off of beamsplitter 260 and into detection system 210. If such light reached the detector 280, the noise floor could be raised, and in the worst case, the signal could be swamped out. For those systems where the illumination light and the detection light are orthogonally polarized, most of the light reflecting from spatial light modulator array 300 would return to the illumination system 205, and any residual leaking into the detection channel could be eliminated by the polarization analyzer 255. Alternately, if the system is being used to detect fluorescent light, and the system includes a filter, then this filter can likewise remove illumination light leakage from back reflections from spatial light modulator array 300 (and other surfaces). This problem could also be reduced if the off state pixels of spatial light modulator array 300 absorbed, rather than retro-reflected, the incident illumination light.

Figure 5:
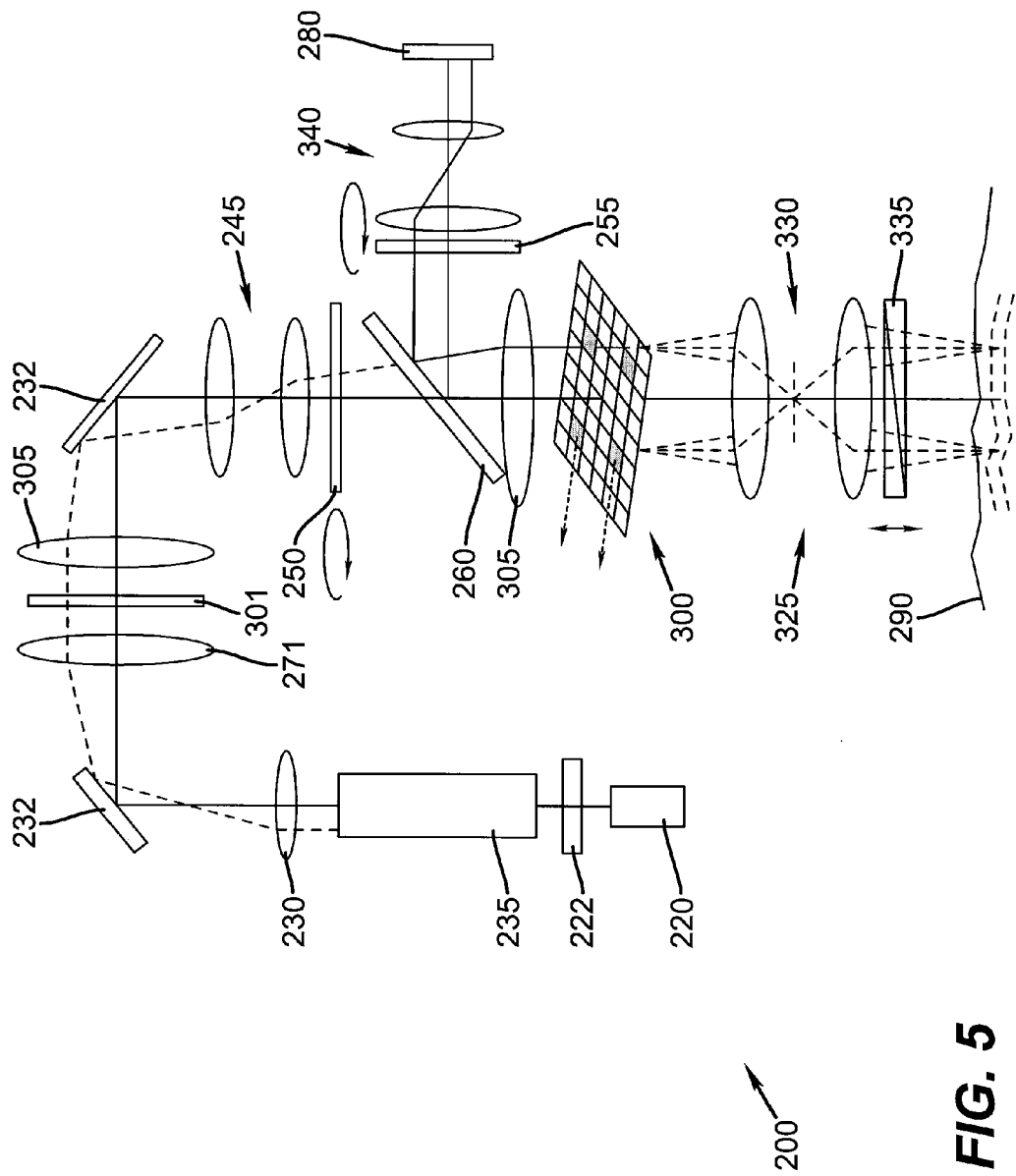
FIG. 5 is a cross sectional view of an alternate embodiment for a tissue imaging system of the present invention.

The system of FIG. 4*a*, in all its variations, has been described as employing an illumination system that provides flood illumination the spatial light modulator array 300. Alternate embodiments are possible in which spatial light modulator array 300 is addressed with beams of illumination light, rather than being flood illuminated. One such example is shown in FIG. 5, wherein an illumination system with an integrating bar 235, condenser lens 230, and illumination field lens 271, is used to flood illuminate a second modulator array 301. Nominally, this second array 301 is telecentrically imaged by an illumination relay lens system 245 to spatial light modulator array 300. Modulator array 300 and second modulator array 301 can be identical devices, with the illumination relay lens system 245 operating at unity (1:1) magnification. The two modulators could then be addressed identically by a controller, so that the a given pixel of second modulator array 301 transmits a beam illumination light, which is then re-imaged to a corresponding pixel on spatial light modulator array 300. As spatial light modulator array 300 is no longer flood illuminated, but is only illuminated by addressed beams of light, the off state pixels should no longer retro-reflect intense illumination light which may otherwise leak into the detection channel. The tissue imaging system 200 of FIG. 5 could also have multi-modal operation. For example, if all pixels of both modulator arrays 300 and 305 were simultaneously driven to an on-state, tissue 290 would be flood illuminated, and tissue imaging system 200 could again operate as a camera or microscope. Of course, by adding a second modulator array 301 and an illumination relay lens system 245 to the tissue imaging system 200, the system is then burdened with additional cost, complexity, and size.

On the other hand, it is possible that second modulator array 301 could be replaced with an addressable array light source, such as a laser array light source (which, for example, could be a VCSEL array, an organic laser array, or a quantum dot laser array) or an LED array. The addressable array light source could address the spatial light modulator array 300 pixels with 1:1 correspondence, or could address a multitude, with one light emitter per N pixels, or visa-versa. In that case, the same functionality would be provided, but the system size could be reduced, as the light integration portion of the illumination system could be eliminated.

Figure 6:
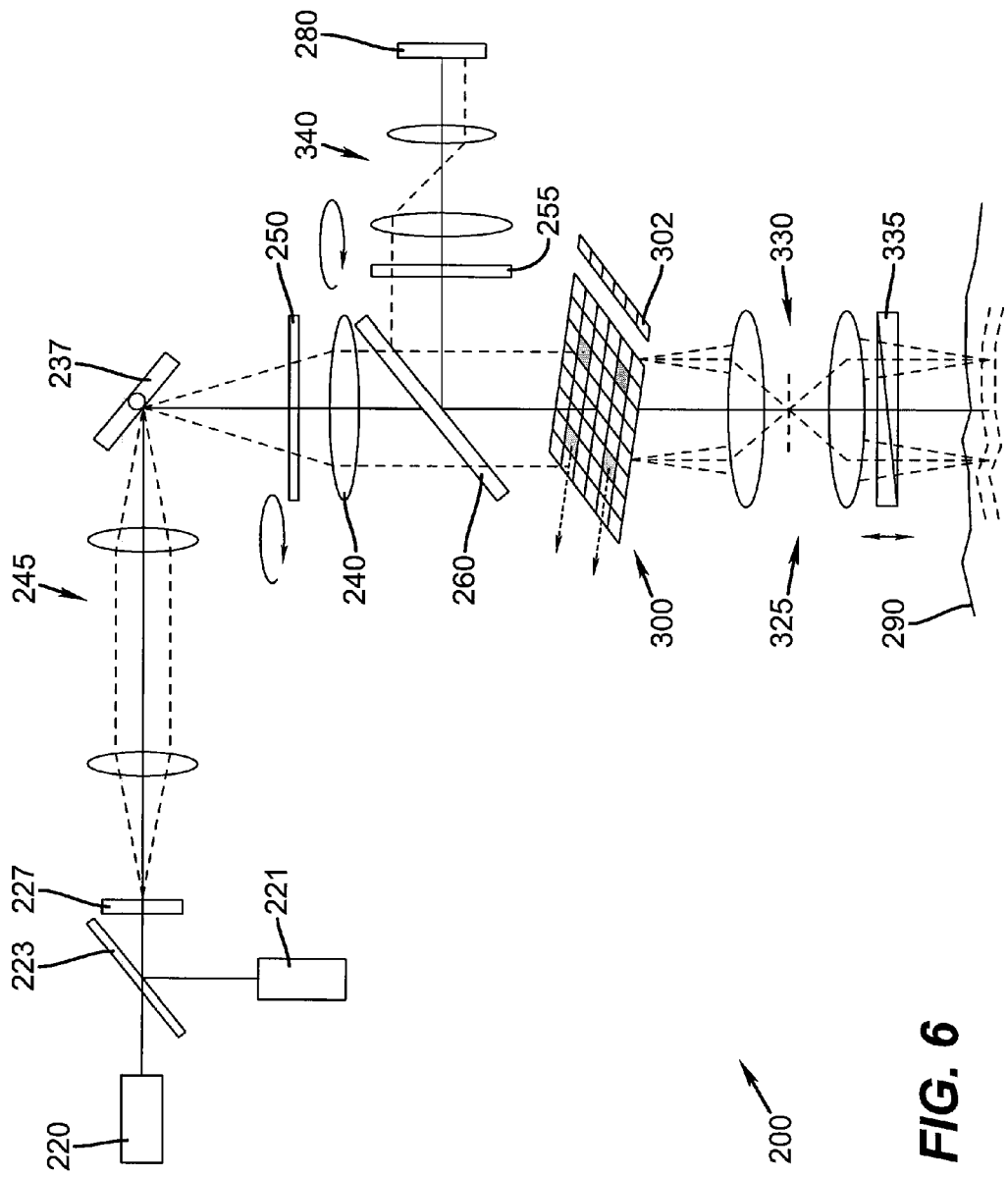
FIG. 6 is a cross sectional view of an alternate embodiment for a tissue imaging system of the present invention.

As another alternative to addressing the same potential problem of optically addressing spatial light modulator array 300 with light beams, the tissue imaging system 200 of FIG. 6 depicts a configuration in which the illumination system has a light source 220 that directs a light beam to a multi-beam generator 227. This generator could be an active device, such as an acousto-optic modulator, or a passive device, such as 1:N linear or area beamsplitter. The resulting beams are directed by an illumination relay lens 245 onto a scanning deflector 237 (such as a galvanometer, or a dual galvanometer arrangement). The scanning beams are redirected by illumination field lens 240, so that these illumination beams are incident in a nominally telecentric fashion to spatial light modulator array 300. In combination, multi-beam generator 227 and scanning deflector 237 scan an array of light beams across the input side of spatial light modulator array 300, thereby addressing some number of modulator pixels at any given time. A line start sensor 302 could be provided adjacent to spatial light modulator array 300, to enable detection of the scanning light beams, so that the scanning of the light beams can be synchronized with the addressing of the modulator pixels. Although the FIG. 6 imaging system can provide optically addressed illumination light beams with greater light efficiency than does the system of FIG. 5, this approach is encumbered with more moving parts and the issues of timing and synchronization.

To another point, the system of FIG. 6 shows that the illumination system can be provided with at least a second light source 221. This second light source would have a different spectral output than does light source 220. The emitted beams from the two light sources can be combined, for example by means of a dichroic filter 223, so that the two beams than traverse nominally common optical paths through the rest of the illumination system. Of course, this same approach to providing multiple different wavelength light sources could be applied to the systems of FIGS. 4 and 5. Considering again the system of FIG. 4*a*, as another alternative, instead of one light source 220, a multitude of different spectral light sources could be arrayed about the light source 220 that is shown. Each of these light sources could be directed so that their beams go directly into integrating bar 235, or go into integrating bar 235 after first encountering diffuser 222. As a result, the field of uniform illumination that is provided to a modulator array (300 or 301) can readily be made spectrally variable without sacrificing illumination uniformity.

The previously described tissue imaging systems 200 of FIGS. 4*a*-4*e*, 5, and 6 all are nominally designed using confocal imaging principles, with a spatial light modulator array 300 that provides a variable array of programmable pinholes. Moreover, in all of these systems, the spatial light modulator array 300 is located in the tissue-imaging portion of the design, between the beamsplitter 260 and the objective lens 325. As a result, spatial light modulator array 300 has a dual use, in which it provides pinhole functionality for both the illumination light and the image light. However, within the field of confocal imaging, there are numerous scanning confocal microscopes, which generally use lasers to provide focused beams of light to the tissue sample. In effect, the laser source acts like its own illumination pinhole. Then only one physical pinhole is needed, in the detection channel. Following this logic, the tissue imaging system depicted in FIG. 7 has modulator array 300 in the detection channel 210. The objective lens 325 effectively has a split design, with part of it residing on the tissue side of beamsplitter 260, and another part (shown simply as modulator field lens 305) in the detection channel 210, prior to modulator array 300. This version of system 200 then has a laser scanning illumination system 205, which can be similar to that of the system of FIG. 6, except that the illuminating beams may not approach beamsplitter 260 telecentrically, but are generally focused into beamsplitter 260, as beamsplitter 260 can be located in the aperture stop of objective lens 325. While the beamsplitter 260 can be smaller than in the prior systems, the design of objective lens 325 will likely be more difficult.

Figure 7:
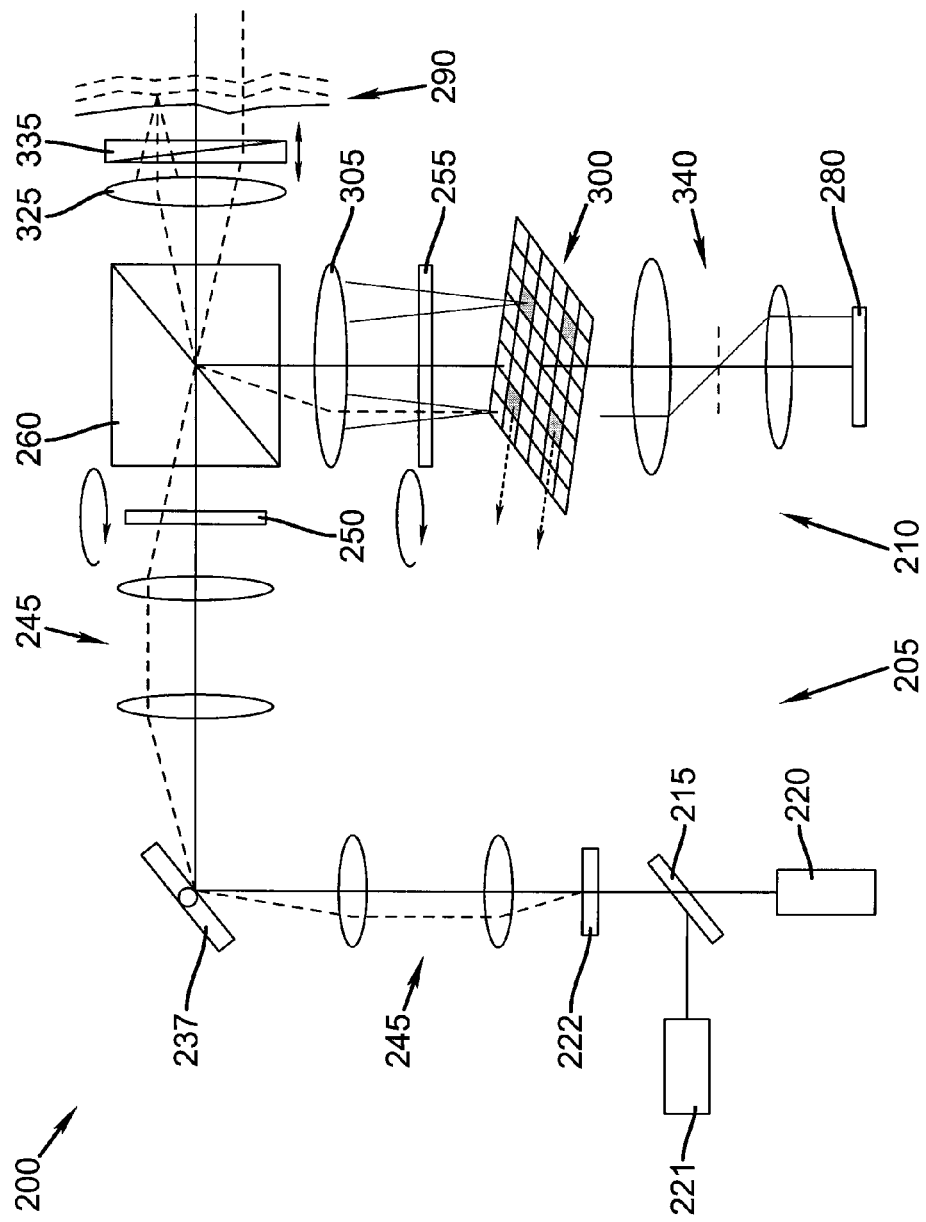
FIG. 7 is a cross sectional view of an alternate embodiment for a tissue imaging system of the present invention.

The tissue imaging systems of the present invention, and particularly those of FIGS. 5, 6, and 7, which are scanning systems, could be used to provide other medical imaging modalities. The systems of these figures have been described relative to having some number of pixels on modulator array 300 each simultaneously illuminated by a corresponding illumination beam, originating from a prior modulator (FIG. 5) or a laser scanning system (FIGS. 6 and 7). Each pixel of spatial light modulator array 300 than corresponds to a beam of light that illuminates a tissue 290 and then a return beam that is redirect to the detection sub-system 210. However, around each spot illuminated in tissue 290, there is a halo of scattered light. This light corresponds to incident photons that have multiply scattered and diffused along different optical paths, with different propagation times. Accordingly, if this scattered light is collected in a spatially sampling manner, then a model of the propagation physics can be used to infer the localized optical properties (scattering and absorption) of the illuminated tissue. This technique is applied in an approach generally known as diffuse optical tomography (DOT), in which an array of sources illuminates the tissue (generally with IR light) and an array of detectors collects the light, with time domain of frequency domain analysis being used to extract the data. In such systems, the light source is typically pulsed or modulated (at ~100 MHz). Exemplary systems include the pulse oximeter of U.S. Pat. No. 5,782,237 (Casciani et al.) and the breast examination system of U.S. Pat. No. 5,353,799 (Chance). An alternate approach, described in part in U.S. Pat. No. 6,577,884 (Boas), has a system with modulated (2 kHz) CW light sources, wherein tissue structural information is extracted from intensity and travel time data. Diffuse optical tomography is used to examine and image shallow sub-surface tissues (such as the epidermis), with application in detecting tumors in the breast and non-invasively determining hemoglobin concentration, hemoglobin oxygen saturation, cytochromes, lipids and water in vivo. Although diffuse optical tomography is not a deep tissue imaging modality, this functionality could still be useful in the device of the present invention.

Figure 8:
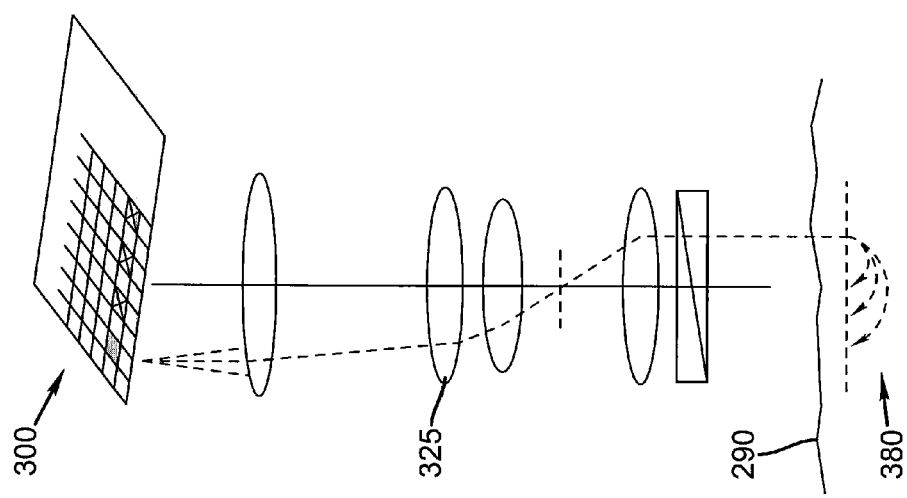
FIG. 8 is a view of an alternate application for a tissue imaging system of the present invention that provides diffuse optical tomography operation.

Typically, DOT systems often involve the use of fixed fiber optic array, with a source fiber and a surrounding arrangement of detection fibers, or a manually applied multiple source and multiple detector configuration. Thus, there could be value in having a programmable tissue imaging system capable of diffuse optical tomography. In particular, the systems of FIGS. 5, 6, and 7 of this application might be extended to provide a diffuse optical tomography imaging modality, if a given modulator pixel of modulator 300 was used for illumination, while some number of adjacent pixels were used for detection. In this case, the adjacent pixels would be operated to an On-state, but would not receive a direct illumination beam. For clarity, this is depicted in FIG. 8, where the illuminating beam causes multiple diffused light paths 380 in tissue 290. As the diffused light emerges from tissue 290, a portion of it can be re-imaged to corresponding pixels (marked by an "X" in FIG. 8) of spatial light modulator array 300. This light can then be redirected into the detection system 210 (not shown in FIG. 8). To support this imaging modality, light source 220 in tissue imaging system 200 would need to be modulated for data synchronization and extraction with respect to detector 280. It is noted that this approach may have less signal to noise discrimination than typical DOT systems that have the illumination and detection optical fibers in contact with the tissue.

Figure 9:
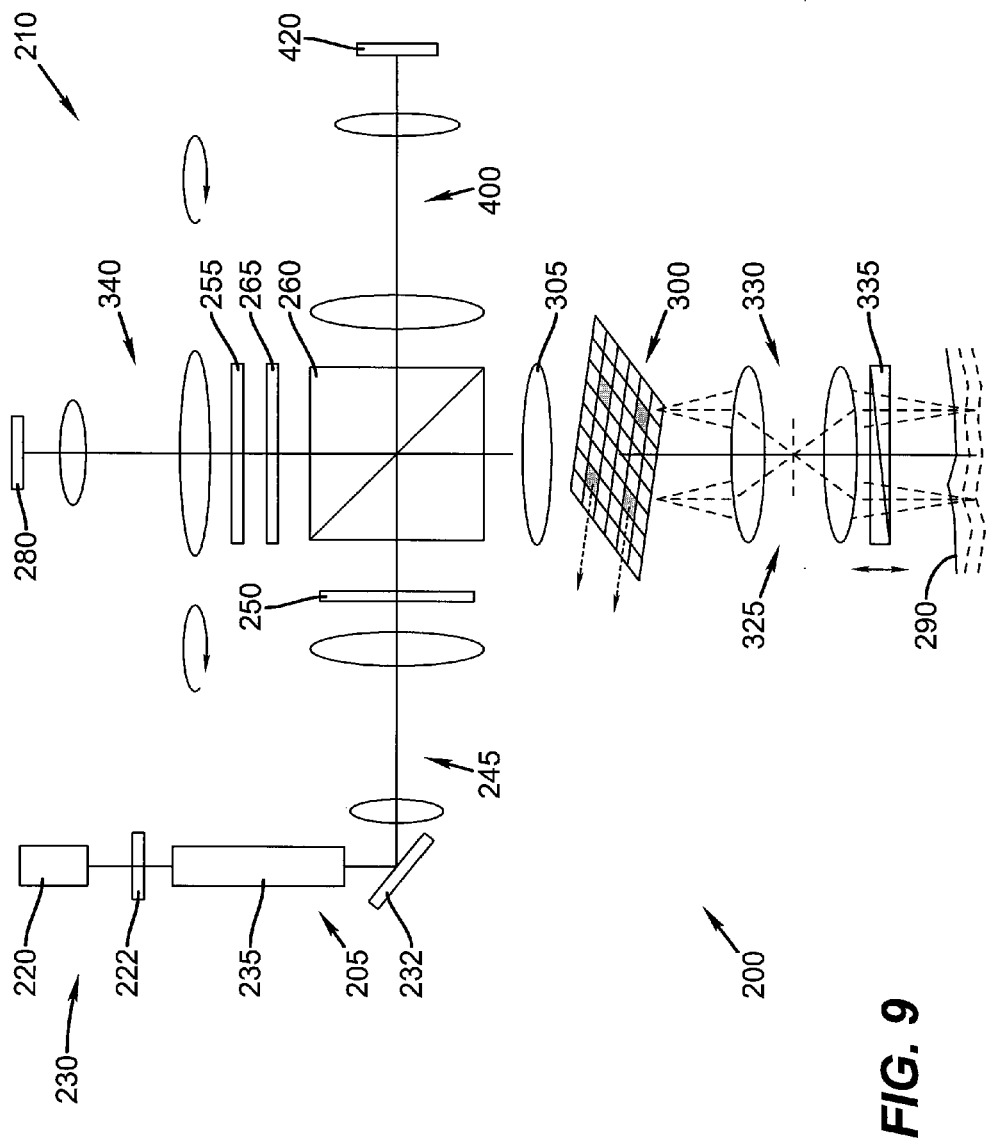
FIG. 9 is a view of alternate embodiments of a tissue imaging system of the present invention that are provided with optical coherence tomography capabilities.
Figure 10:
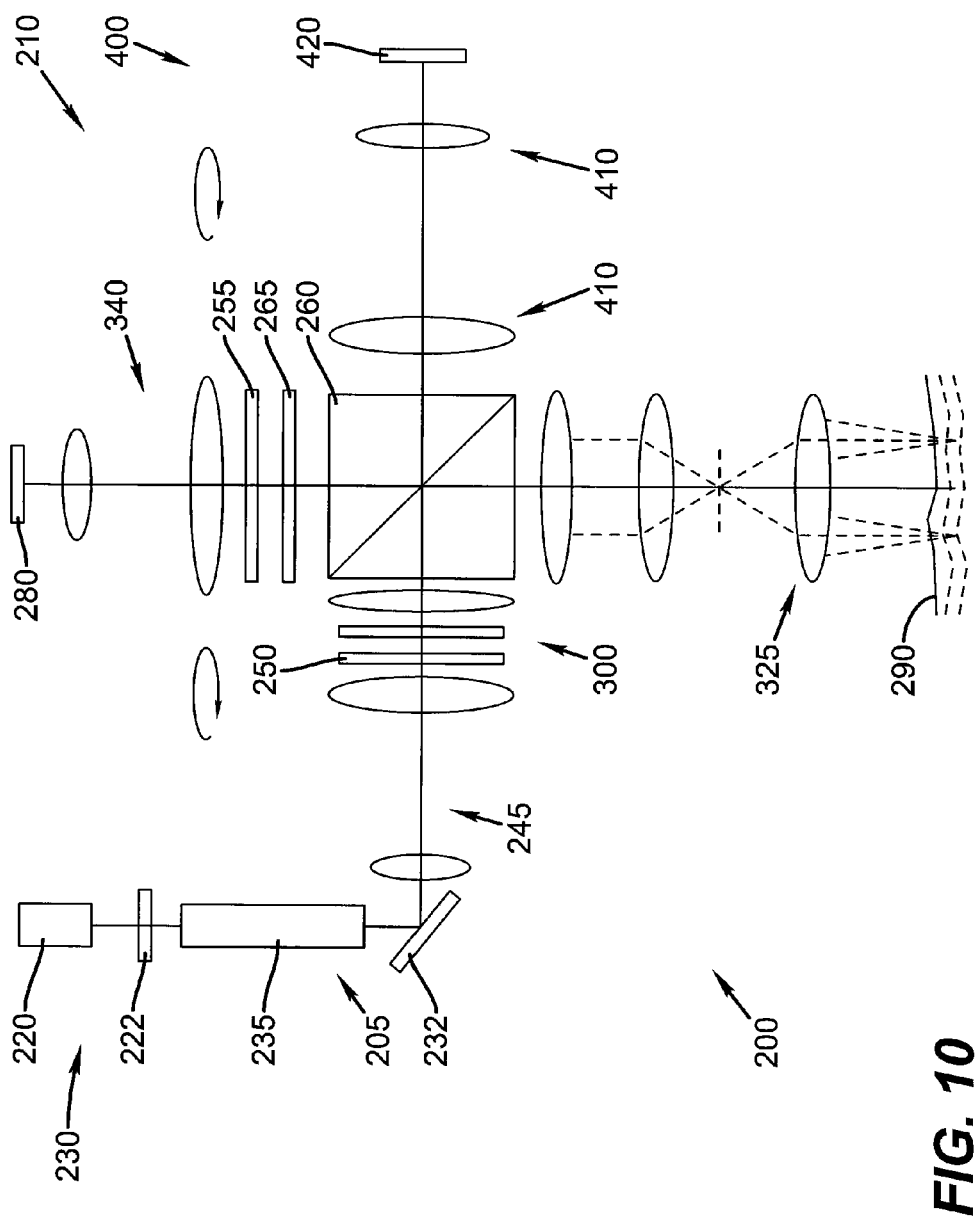
FIG. 10 is a view of an alternate embodiment of a tissue imaging system of the present invention that employs a digital mirror device (DMD) modulator.

The multi-use, deep tissue targeted, tissue imaging system 200 of the present invention could also be designed with optical coherence tomography capability, as depicted in FIGS. 9 and 10. As shown in FIG. 9, the tissue imaging system 200 has a reference system 400, comprising a reference lens 410 and a positionally modulated reference mirror 420, which is positioned off the other side of the beamsplitter 260 and which enables the interference effect required for OCT. The reference mirror would be mechanically driven along the local optical axis by an actuator (such as a piezo or acoustic device, not shown). Reference lens 400 would nominally be identical to objective lens 325. Light source 220 would have the appropriate coherence for OCT operation, and could for example, be an SLD. If all the pixels of spatial light modulator array 300 are simultaneously driven to the open state, then this configuration has some similarities to the wide field of view OCT system described by the prior art Dubois '602 patent, and tissue imaging system 200 could potentially operate in a standard OCT imaging modality. However, if the spatial light modulator array 300 is operated to act like a programmable pinhole array, for example with select non-adjacent pixels open, then the tissue imaging system 200 could provide a combined complimentary-effect confocal/OCT imaging effect. This offers several potential advantages. To begin with, it has been shown in a paper by Xu et al.; "*Confocal Enhanced Optical Coherence Tomography for Nondestructive Evaluation of Paints and Coatings*" Optics Letters, Vol. 24, No. 24, 1999, pp. 1808-1810, that the simultaneous combination of confocal imaging and OCT imaging, with a pinhole enhancing the interference discrimination of OCT, can provide improved resolution and contrast. However, the system of Xu et al. used a single-point scanning beam. By comparison, the system of FIG. 9 could provide a combined confocal/OCT imaging modality with both a wide field of view and the programmable flexibility enabled by the spatial light modulator array 300, without having to mechanically scan beams across the tissue sample 290. Tissue imaging system 200 of FIG. 9 could also provide standard confocal imaging by disabling the reference system 400. Tissue imaging system 200 could also be operated sequentially, shifting from confocal-only, to OCT-only, to combined confocal/OCT operation in some operational sequence. The tissue imaging system 200 could also function as a camera or microscope by disabling the reference system 400 and operating all pixels 310 of spatial light modulator array 300 in an on-state. Additionally, the system of FIG. 9 also can be equipped with polarizers 250 and 255 to enable polarization sensitive imaging. Furthermore, the combination of an objective lens 325 (preferably telecentric) with a focus mechanism 335 could further enhance the imaging capability over traditional OCT, by enabling sample arm depth scanning, in which the zone of best focus could be adjusted to different depths within tissue 290. Finally, the tissue imaging system 200 of FIG. 9 could also have multiple light sources and/or spectral filters to enable multi-spectral or fluorescence imaging.

As previously noted, the imaging of a medical OCT system, relative to resolution, imaging depth, and signal strength, is dependent on the light scattering characteristics of the tissues being examined. Thus, in the case of granulation tissue, which might be considered a moderately scattering media, with a scattering coefficient $\mu_s \sim 1.8$ mm$^{-1}$, an optical imaging depth of ~4-5 mm for IR light could be anticipated, which extends the utility of the device for "deep" tissues imaging. Other means for extending the imaging depth of OCT systems, such as the use of axicons may also be employed with this system.

The system of FIG. 10 is a variation on that of FIG. 9, where spatial light modulator array 300 is provided in the illumination system 205, rather than just prior to objective lens 325. In this case, tissue imaging system 200 could provide an enhanced OCT imaging modality, with addressablity and a wide field of view, but without the potential resolution, contrast, and imaging depth enhancements of the FIG. 9 system. A further system configuration can also be anticipated, which would resemble that of FIG. 9, with a spatial light modulator array 300 between beamsplitter 260 and objective lens 325, but which would further have a second modulator array in the illumination system, much as depicted in FIG. 5. With such an approach, the programmable wide field of view combined confocal/OCT imaging capability would be further equipped with illumination light beam pixel addressability, which could further enhance the signal to noise capability of the system.

Figure 11:
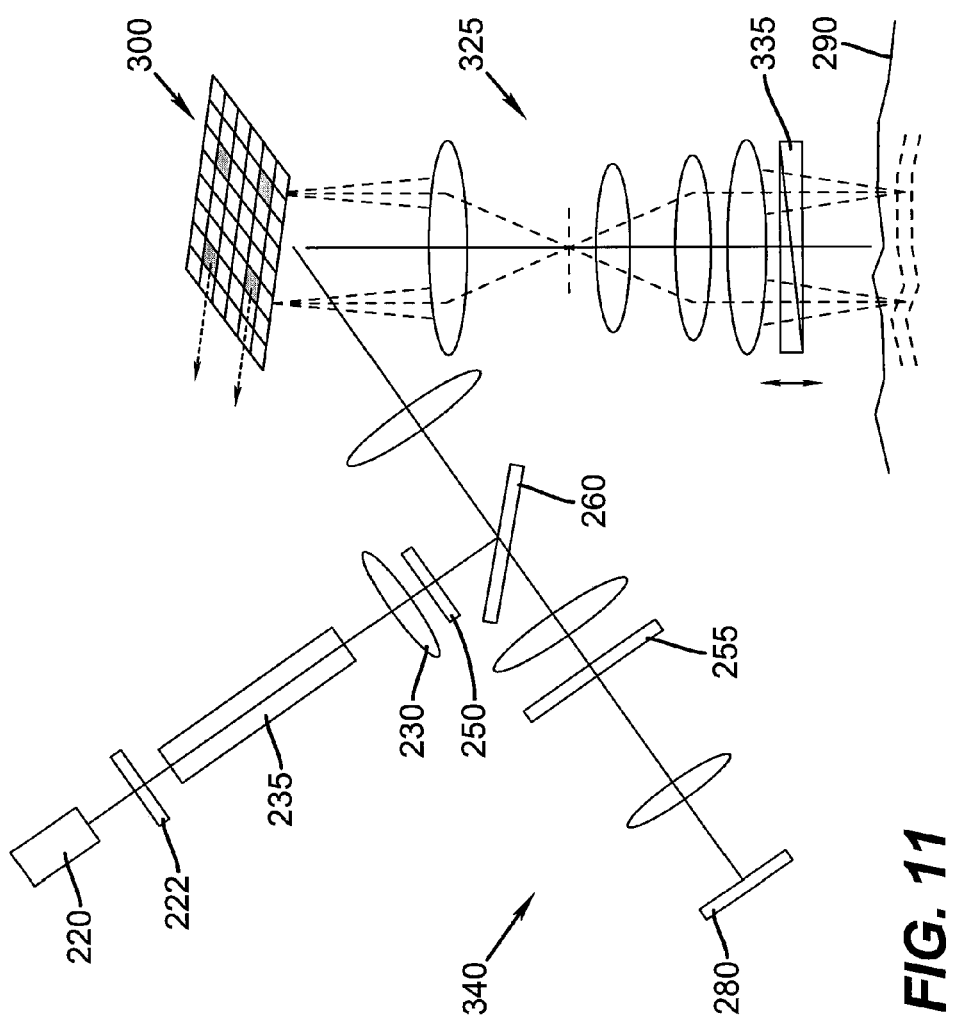
FIG. 11 is a schematic view of yet another embodiment of a tissue imaging system according to the present invention.

Finally, another alternate configuration is depicted in FIG. 11, in which spatial light modulator array 300 is a reflective device, such as a digital micro-mirror device (DMD). Like the prior systems, this system has polarizers 250 and 255, telecentric objective lens 325, and focus mechanism 335. However, the overall system configuration is more cumbersome than the preferred configuration (FIG. 4a) with a transmissive modulator array.

The invention has been described in detail with particular reference to certain preferred embodiments thereof, but it will be understood that variations and modifications can be effected within the scope of the invention. For example, it should be understood that the devices of the present invention could be used for applications other than medical imaging, such as for the non-destructive examination of manufactured devices, components, or coatings.

PARTS LIST 100 skin
105 epidermis
110 dead epithelial cells
115 basement membrane (basal lamina)
120 reticular dermis
125 blood capillary
127 red blood cells
130 proteoglycans
140 fibroblasts
145 collagen fiber bundles
160 human body
165 Langer's cleavage lines
200 tissue imaging system
205 illumination system
210 detection system
220 light source
221 second light source
222 diffuser
223 dichroic filter
225 light emitters
227 multi-beam generator
230 condenser lens
232 mirror
235 integrating bar
237 scanning deflector
240 illumination field lens
245 illumination relay lens
247 illumination optical axis
250 pre-polarizer
252 waveplate
255 polarization analyzer
257 wire grid polarization beamsplitter
260 beamsplitter
265 waveplate
270 objective lens
271 illumination field lens
275 imaging field lens
277 imaging optical axis
280 detector (sensor array)
290 tissue
300 spatial light modulator array
301 second modulator array
302 line start sensor
305 modulator field lens
310 modulator pixel
325 objective lens
330 aperture stop
332 pupil filter
335 focus mechanism
340 imaging lens
345 first lenslet array
350 second lenslet array
355 field lenslet array
360 controller
370 housing
375 support
380 diffused light paths
400 reference system
410 reference lens
420 reference mirror

The invention claimed is:

1. A tissue imaging system for imaging optically examining the medical condition of tissue comprising:
   a) an illumination optical system, comprising a light source, having one or more light emitters, beam shaping optics, and polarizing optics, which together provide illumination light;
   b) an optical beamsplitter which accepts illumination light from said illumination system and directs it to an imaging sub-system;
   c) a spatial light modulator array within said imaging sub-system;
   d) an objective lens with a focus control means for imaging illumination light from said spatial light modulator array to said tissue and for collecting image light from said tissue and imaging said image light to said spatial light modulator array;
   e) an optical detection system, comprising focusing optics and polarizing optics which image said spatial light modulator to an optical detector array;
   f) a controller which drives said spatial light modulator to provide time variable arrangements of on-state pixels, wherein each of said on-state pixels transmits beams of said illumination light;
   wherein said objective lens operates in a nominally telecentric manner relative to both said spatial light modulator and to said tissue;
   wherein said polarizing optics, provided in said illumination optical system and said optical detection system, are independently and iteratively rotated so as to define variable polarization states relative to said tissue; and
   wherein said spatial light modulator array is operated such that the modulator pixels optically function like pinholes relative to said illumination light and said image light.

2. A system as in claim 1 wherein said focus means is an optical device operating in telecentric optical space between said objective lens and said tissue.

3. A system as in claim 1 wherein said controller is provided for operating at least said light source, said detector array, said focus control, and said rotational motion of said polarizers.

4. A system as in claim 1 wherein said polarizing optics, provided in both said illumination optical system and said optical detection system, are crossed so as to pass orthogonal polarization states.

5. A system as in claim 1 wherein said polarizing optics, provided in either or both said illumination optical system and said optical detection system, include wire grid polarizers.

6. A system as in claim 1 wherein said polarizing optics, provided in either or both said illumination optical system and said optical detection system, include a wave plate.

7. A system as in claim 1 wherein said illumination optical system includes an optical uniformizer for homogenizing said illumination light.

8. A system as in claim 1 wherein said spatial light modulator array is operated such that the modulator pixels optically function like pinholes relative to said illumination light and said image light.

9. A system as in claim 8 wherein said system operates in a confocal imaging modality.

10. A system as in claim 1 wherein said focus means comprises an assembly of opposing wedge prisms which are slid laterally relative to each other, to alter the optical path length of the transiting illumination and imaging light.

11. A system as in claim 1 wherein said focusing optics of said optical detection system includes an arrangement of lenslet arrays to sample and image said image light onto said optical detector array.

12. A system as in claim 1 wherein said objective lens includes a pupil plane filter located at an aperture stop plane.

13. A system as in claim 1 wherein said spatial light modulator array is a MEMS device or a LCD device.

14. A system as in claim 1 wherein said light source comprises at least one of he following; a laser, a super-luminescent diode, an LED, or a lamp.

15. A system as in claim 1 wherein said illumination light comprises light in one spectral band and said image light comprises light in a second spectral bad.

16. A system as in claim 1 wherein said illumination light excites a fluorescence in said tissue, producing an emission light, a portion of which comprises said image light.

17. A system as in claim 1 wherein said system is assembled into a housing which includes supports for providing a stable mechanical interaction with said tissue.

18. A tissue imaging system for imaging optically examining the medical condition of tissue comprising:
a) an illumination optical system, comprising a light source, having one or more light emitters, beam shaping optics, which together provide illumination light;
b) an optical beamsplitter which accepts illumination light from said illumination system and directs it an imaging sub-system;
c) a spatial light modulator array within said imaging sub-system;
d) an objective lens with a focus control means for imaging illumination light from said spatial light modulator array to said tissue and for collecting image light from said tissue and imaging said image light to said spatial light modulator array;
e) an optical detection system, comprising focusing optics which image said spatial light modulator to an optical detector array;
f) a controller which drives said spatial light modulator to provide time variable arrangements of on-state pixels, wherein each of said on-state pixels transmits beams of said illumination light;
wherein said objective lens operates in a nominally telecentric manner relative to both said spatial light modulator and to said tissue; and
wherein said spatial light modulator array is operated such that the modulator pixels optically function like pinholes relative to said illumination light and said image light.

19. A system as in claim 18 wherein said focus control means is an optical device operating in telecentric optical space between said objective lens and said tissue.

20. A system as in claim 18 wherein said focus control means comprises a mechanism utilizing two wedge plates to control the optical path length in telecentric optical space.

21. A system as in claim 18 wherein said controller is provided for operating at least said light source, said detector array, said focus control, and for providing image processing of the captured images to aid the diagnostic process.

22. A system as in claim 18 wherein said spatial light modulator array is operated such that the modulator pixels optically function like pinholes relative to said illumination light and said image light.

23. A system as in claim 22 wherein said system operates in a confocal imaging modality.

24. A system as in claim 18 wherein a reference arm, comprising a reference imaging lens and a reference mirror, is provided, to enable said system to operate in an optical coherence tomography imaging modality or a combination confocal imaging and optical coherence tomography imaging modality.

25. A system as in claim 18 wherein said spatial light modulator array is operated in a state where all pixels are open, thereby enabling said system to operate as a digital photographic image capture device.

26. A tissue imaging system for imaging optically examining the medical condition of tissue comprising:
a) an illumination optical system, comprising a light source, having one or more light emitters, beam shaping optics, and polarizing optics, which together provide illumination light;
b) an optical beamsplitter which accepts illumination light from said illumination system and directs it an imaging sub-system;
c) a spatial light modulator array within said imaging sub-system;
d) an objective lens with a focus control means for imaging illumination light from said spatial light modulator array to said tissue and for collecting image light from said tissue and imaging said image light to said spatial light modulator array;
e) an optical detection system, comprising focusing optics and polarizing optics which image said spatial light modulator to an optical detector array;
f) a controller which drives said spatial light modulator to provide time variable arrangements of on-state pixels, wherein each of said on-state pixels transmits beams of said illumination light;
wherein said polarizing optics, provided in said illumination optical system and said optical detection system, are independently and iteratively rotated so as to define variable polarization states relative to said tissue; and wherein said spatial light modulator array is operated such that the modulator pixels optically function like pinholes relative to said illumination light and said image light.

27. A system as in claim 26 wherein said polarizing optics, provided in both said illumination optical system and said optical detection system, are crossed so as to pass orthogonal polarization states.

28. A system as in claim 26 wherein said controller is provided for operating at least said light source, said detector array, said focus control, and said rotational motion of said polarizers.

29. A system as in claim 26 wherein a reference arm, comprising a reference imaging lens and a reference mirror, is provided, to enable said system to operate in an optical coherence tomography imaging modality or a combination confocal imaging and optical coherence tomography imaging modality.

30. A system as in claim 26 wherein said spatial light modulator array is operated in a state where all pixels are open, thereby enabling said system to operate as a digital photographic image capture device.

31. An optical imaging system for examining a sample comprising:
   a) an illumination optical system, comprising a light source, having one or more light emitters, beam shaping optics, and polarizing optics, which together provide illumination light;
   b) an optical beamsplitter which accepts illumination light from said illumination system and directs it an imaging sub-system;
   c) a spatial light modulator array within said imaging sub-system;
   d) an objective lens with a focus control means for imaging illumination light from said spatial light modulator array to said sample and for collecting image light from said sample and imaging said image light to said spatial light modulator array;
   e) an optical detection system, comprising focusing optics and polarizing optics which image said spatial light modulator to an optical detector array;
   f) a controller which drives said spatial light modulator to provide time variable arrangements of on-state pixels, wherein each of said on-state pixels transmits beams of said illumination light;
   wherein said objective lens operates in a nominally telecentric manner relative to both said spatial light modulator and to said sample;
   wherein said polarizing optics, provided in said illumination optical system and said optical detection system, are independently and iteratively rotated so as to define variable polarization states relative to said tissue; and
   wherein said spatial light modulator array is operated such that the modulator pixels optically function like pinholes relative to said illumination light and said image light.

32. A system as in claim 31 wherein said controller is provided for operating at least said light source, said detector array, said focus control, and said rotational motion of said polarizers.

33. A system as in claim 31 wherein said focusing optics of said optical detection system includes an arrangement of lenslet arrays to sample and image said image light onto said optical detector array.

34. A system as in claim 31 wherein said focus control means comprises a mechanism utilizing two wedge plates to control the optical path length in telecentric optical space.

35. A system as in claim 31 wherein said operation of said spatial light modulator array such that said modulator pixels optically function like pinholes relative to said illumination light and said image light enables a confocal imaging modality.

36. A system as in claim 31 wherein said spatial light modulator array is operated in a state where all pixels are open, thereby enabling said system to operate as a digital photographic image capture device.

37. A system as in claim 31 wherein a reference arm, comprising a reference imaging lens and a reference mirror, is provided, to enable said system to operate in an optical coherence tomography imaging modality or a combination confocal imaging and optical coherence tomography imaging modality.

38. A system as in claim 31 wherein said illumination light comprises light in one spectral band and said image light comprises light in a second spectral bad.

39. A system as in claim 31 wherein said illumination light excites a fluorescence in said tissue, producing an emission light, a portion of which comprises said image light.

40. A tissue imaging system for imaging optically examining the medical condition of tissue comprising:
   a) an illumination optical system, comprising a light source, having one or more light emitters, beam shaping optics, polarizing optics, and an optical addressing means, which together provide illumination light;
   b) an optical beamsplitter which accepts illumination light from said illumination system and directs it an imaging sub-system;
   c) a spatial light modulator array within said imaging sub-system;
   d) an objective lens with a focus control means for imaging illumination light from said spatial light modulator array to said tissue and for collecting image light from said tissue and imaging said image light to said spatial light modulator array;
   e) an optical detection system, comprising focusing optics and polarizing optics which image said spatial light modulator to an optical detector array;
   f) a controller which drives said spatial light modulator to provide time variable arrangements of on-state pixels, wherein each of said on-state pixels transmits beams of said illumination light;
   wherein said objective lens operates in a nominally telecentric manner relative to both said spatial light modulator and to said tissue; and
   wherein said polarizing optics, provided in said illumination optical system and said optical detection system, are independently and iteratively rotated so as to define variable polarization states relative to said tissue.

41. A system as in claim 40 wherein said spatial light modulator array is operated such that the modulator pixels optically function like pinholes relative to said illumination light and said image light.

42. A system as in claim 41 wherein said system operates in a confocal imaging modality.

43. A system as in claim 41 wherein a first quantity of said modulator pixels are simultaneously driven to said on-state and are addressed with illumination light, and a second quantity of said modulator pixels proximate to each of said first quantity of modulator pixels are also driven to an on-state.

44. A system as in claim 43 wherein said system operates in a diffuse optical imaging modality.

45. A system as in claim 40 wherein a reference arm, comprising a reference imaging lens and a reference mirror, is provided, to enable said system to operate in an optical coherence tomography imaging modality or a combination confocal imaging and optical coherence tomography imaging modality.

46. A system as in claim 40 wherein said optical addressing means is a second spatial light modulator array or a multi-beam generator.

47. A system as in claim 46 wherein both said spatial light modulator array of said imaging subsystem and said second spatial light modulator array are simultaneously operated in a state where all pixels are open, thereby enabling said system to operate as a digital photographic image capture device.

48. A system as in claim 40 wherein said light source is an array of said multiple emitters configured to provide said addressing means of said spatial light modulator array, with a given emitter illuminating a subset of one or more of said modulator pixels.

49. A system as in claim 40 wherein said focus means is an optical device operating in telecentric optical space between said objective lens and said tissue.

50. A system as in claim 40 wherein said controller is provided for operating at least said light source, said detector array, said focus control, and said rotational motion of said polarizers.

51. A system as in claim 40 wherein said polarizing optics, provided in both said illumination optical system and said optical detection system, are crossed so as to pass orthogonal polarization states.

52. A system as in claim 40 wherein said polarizing optics, provided in both said illumination optical system and said optical detection system, include wire grid polarizers.

53. An optical imaging system for optically examining a sample comprising:
   a) an illumination optical system, comprising a light source, having one or more light emitters, beam shaping optics, polarizing optics, and an optical addressing means, which together provide illumination light;
   b) an optical beamsplitter which accepts illumination light from said illumination system and directs it an imaging sub-system;
   c) a spatial light modulator array within said imaging sub-system;
   d) an objective lens with a focus control means for imaging illumination light from said spatial light modulator array to said sample and for collecting image light from said sample and imaging said image light to said spatial light modulator array;
   e) an optical detection system, comprising focusing optics and polarizing optics which image said spatial light modulator to an optical detector array;
   f) a controller which drives said spatial light modulator to provide time variable arrangements of on-state pixels, wherein each of said on-state pixels transmits beams of said illumination light; and
   wherein said polarizing optics, provided in said illumination optical system and said optical detection system, are independently and iteratively rotated so as to define variable polarization states relative to said sample.

54. A system as in claim 53 wherein said spatial light modulator array is operated such that the modulator pixels optically function like pinholes relative to said illumination light and said image light.

55. A system as in claim 54 wherein said system operates in a confocal imaging modality.

56. A system as in claim 54 wherein a first quantity of said modulator pixels are simultaneously driven to said on-state and are addressed with illumination light, and a second quantity of said modulator pixels proximate to each of said first quantity of modulator pixels are also driven to an on-state.

57. A system as in claim 56 wherein said system operates in a diffuse optical imaging modality.

58. A system as in claim 53 wherein a reference arm, comprising a reference imaging lens and a reference mirror, is provided, to enable said system to operate in an optical coherence tomography imaging modality or a combination confocal imaging and optical coherence tomography imaging modality.

59. A system as in claim 53 wherein said optical addressing means is a second spatial light modulator array or a multi-beam generator.

60. A system as in claim 53 wherein said light source is an array of said multiple emitters configured to provide said addressing means of said spatial light modulator array, with a given emitter illuminating a subset of one or more of said modulator pixels.

61. An optical imaging system for examining a sample comprising:
   a) an illumination optical system, comprising a light source, having one or more light emitters, beam shaping optics, an optical addressing means, which together provide illumination light;
   b) an optical beamsplitter which accepts illumination light from said illumination system and directs it an imaging sub-system;
   c) a spatial light modulator array within said imaging sub-system;
   d) an objective lens with a focus control means for imaging illumination light from said spatial light modulator array to said sample and for collecting image light from said sample and imaging said image light to said spatial light modulator array;
   e) an optical detection system, comprising focusing optics which image said spatial light modulator to an optical detector array;
   f) a controller which drives said spatial light modulator to provide time variable arrangements of on-state pixels, wherein each of said on-state pixels transmits beams of said illumination light; and
   wherein said objective lens operates in a nominally telecentric manner relative to both said spatial light modulator and to said sample.

62. A system as in claim 61 wherein said spatial light modulator array is operated such that the modulator pixels optically function like pinholes relative to said illumination light and said image light.

63. A system as in claim 62 wherein said system operates in a confocal imaging modality.

64. A system as in claim 62 wherein a first quantity of said modulator pixels are simultaneously driven to said on-state and are addressed with illumination light, and a second quantity of said modulator pixels proximate to each of said first quantity of modulator pixels are also driven to an on-state.

65. A system as in claim 64 wherein said system operates in a diffuse optical imaging modality.

66. A system as in claim 61 wherein a reference arm, comprising a reference imaging lens and a reference mirror, is provided, to enable said system to operate in an optical coherence tomography imaging modality, a confocal imaging modality, or a combination confocal imaging and optical coherence tomography imaging modality.

67. A system as in claim 61 wherein said optical addressing means is a second spatial light modulator array or a multi-beam generator.

68. A system as in claim 61 wherein said light source is an array of said multiple emitters configured to provide said addressing means of said spatial light modulator array, with a given emitter illuminating a subset of one or more of said modulator pixels.

69. A system as in claim 61 wherein said focus means is an optical device operating in telecentric optical space between said objective lens and said sample.

70. A system as in claim 61 wherein said objective lens includes a pupil plane filter located at an aperture stop plane.

71. A system as in claim 61 wherein said focusing optics of said optical detection system includes an arrangement of lenslet arrays to sample and image said image light onto said optical detector array.

72. An optical imaging system for examining a sample comprising:
- a) an illumination optical system, comprising a light source, having one or more light emitters and beam shaping optics which together provide illumination light;
- b) an optical beamsplitter which accepts illumination light from said illumination system and directs it an imaging sub-system;
- c) a spatial light modulator array within said imaging sub-system;
- d) an objective lens with a focus control means for imaging illumination light from said spatial light modulator array to said sample and for collecting image light from said sample and imaging said image light to said spatial light modulator array;
- e) a reference arm comprising a lens and a moving mirror;
- f) an optical detection system, comprising focusing optics which image said spatial light modulator to an optical detector array; and
- g) a controller which drives said spatial light modulator to provide time variable arrangements of on-state pixels, wherein each of said on-state pixels transmits beams of said illumination light.

73. A system as in claim 72 wherein said objective lens operates in a nominally telecentric manner relative to both said spatial light modulator and to said sample.

74. A system as in claim 73 wherein said focus means is an optical device operating in telecentric optical space between said objective lens and said sample.

75. A system as in claim 72 wherein said spatial light modulator array is operated such that the modulator pixels optically function like pinholes relative to said illumination light and said image light.

76. A system as in claim 72 which is capable of providing an optical coherence tomography imaging modality, a confocal imaging modality, or a combination confocal imaging and optical coherence tomography imaging modality.

77. A system as in claim 72 wherein said controller is provided for operating at least said light source, said detector array, said focus control, and for providing image processing of the captured images to aid the diagnostic process.

78. A system as in claim 72 wherein said illumination system includes an optical addressing means.

79. A system as in claim 78 wherein said optical addressing means is a second spatial light modulator array or a multi-beam generator.

80. A system as in claim 72 wherein said illumination optical system and said optical detection system both include polarization optics.

81. A system as in claim 80 wherein said polarizing optics are crossed so as to pass orthogonal polarization states.

82. A system as in claim 80 wherein said polarizing optics are independently and iteratively rotated so as to define variable polarization states relative to said sample.

83. An optical imaging system for examining a specimen comprising:
- a) an illumination optical system, comprising a light source, having one or more light emitters and beam shaping optics which together provide illumination light;
- b) an optical beamsplitter which accepts illumination light from said illumination system and directs it an imaging sub-system;
- c) a spatial light modulator array within said imaging sub-system;
- d) an objective lens with a focus control means for imaging illumination light from said spatial light modulator array to said specimen and for collecting image light from said specimen and imaging said image light to said spatial light modulator array;
- e) an optical detection system, comprising focusing optics which image said spatial light modulator to an optical detector array;
- f) a controller which drives said spatial light modulator to provide time variable arrangements of on-state pixels, wherein each of said on-state pixels transmits beams of said illumination light; and
- wherein said focusing optics of said optical detection system includes an arrangement of lenslet arrays to sample and image said image light onto said optical detector array.

84. A system as in claim 83 wherein said focusing optics create an intermediate image, which is sampled and re-imaged by said arrangement of lenslet arrays in a partially overlapping fashion onto said optical detector array.

85. A system as in claim 83 wherein said objective lens operates in a nominally telecentric manner relative to both said spatial light modulator and to said sample.

86. A system as in claim 85 wherein said focus means is an optical device operating in telecentric optical space between said objective lens and said sample.

87. A system as in claim 83 wherein said spatial light modulator array is operated such that the modulator pixels optically function like pinholes relative to said illumination light and said image light.

88. A system as in claim 83 wherein said controller is provided for operating at least said light source, said detector array, said focus control, and for providing image processing of the captured images to aid the diagnostic process.

89. A system as in claim 83 wherein said illumination optical system and said optical detection system both include polarization optics.

90. A system as in claim 89 wherein said polarizing optics are crossed so as to pass orthogonal polarization states.

91. A system as in claim 89 wherein said polarizing optics are independently and iteratively rotated so as to define variable polarization states relative to said sample.

* * * * *